US012616677B2

(12) United States Patent
Valle Colon et al.

(10) Patent No.: US 12,616,677 B2
(45) Date of Patent: May 5, 2026

(54) INJECTABLE PHARMACEUTICAL COMPOSITIONS AND USES THEREOF

(71) Applicant: Intervet Inc., Madison, NJ (US)

(72) Inventors: Brenda L. Valle Colon, New Brunswick, NJ (US); Keith A. Freehauf, Stockton, NJ (US); Frank Guerino, Monroe Township, NJ (US); Christopher D. Kulczar, Jersey City, NJ (US); Brian Carrillo, Jackson, NJ (US)

(73) Assignee: Intervet Inc., Rahway, NJ (US)

( * ) Notice: Subject to any disclaimer, the term of this patent is extended or adjusted under 35 U.S.C. 154(b) by 1165 days.

(21) Appl. No.: 17/606,262

(22) PCT Filed: May 1, 2020

(86) PCT No.: PCT/EP2020/062181
§ 371 (c)(1),
(2) Date: Oct. 25, 2021

(87) PCT Pub. No.: WO2020/225143
PCT Pub. Date: Nov. 12, 2020

(65) Prior Publication Data

US 2022/0296564 A1 Sep. 22, 2022

Related U.S. Application Data

(60) Provisional application No. 62/842,709, filed on May 3, 2019.

(51) Int. Cl.

| | |
|---|---|
| ***A61K 31/365*** | (2006.01) |
| ***A61K 9/00*** | (2006.01) |
| ***A61K 9/16*** | (2006.01) |
| ***A61K 31/42*** | (2006.01) |
| ***A61K 31/422*** | (2006.01) |
| ***A61P 33/00*** | (2006.01) |

(52) U.S. Cl.
CPC .......... *A61K 31/365* (2013.01); *A61K 9/0019* (2013.01); *A61K 9/1617* (2013.01); *A61K 9/1635* (2013.01); *A61K 9/1641* (2013.01); *A61K 9/1652* (2013.01); *A61K 9/1694* (2013.01); *A61K 31/42* (2013.01); *A61K 31/422* (2013.01); *A61P 33/00* (2018.01)

(58) Field of Classification Search
None
See application file for complete search history.

(56) References Cited

U.S. PATENT DOCUMENTS

| | | | |
|---|---|---|---|
| 11,497,732 | B2 | 11/2022 | Le Hir De Fallois et al. |
| 2011/0059988 | A1 | 3/2011 | Heckeroth |
| 2011/0152312 | A1 | 6/2011 | Le Hir de Fallois et al. |
| 2013/0143956 | A1 | 6/2013 | Cady et al. |
| 2016/0235720 | A1 | 8/2016 | Foster et al. |
| 2016/0256442 | A1 | 9/2016 | Cady et al. |
| 2017/0239218 | A1 | 8/2017 | Le Hir De Fallois et al. |
| 2018/0177730 | A1 | 6/2018 | Corace et al. |
| 2020/0022959 | A1 | 1/2020 | Cady et al. |
| 2021/0177808 | A1 | 6/2021 | Freehauf et al. |
| 2021/0299104 | A1 | 9/2021 | Cady et al. |

FOREIGN PATENT DOCUMENTS

| | | | |
|---|---|---|---|
| EP | 0525307 | A1 | 2/1993 |
| EP | 1197207 | B1 | 4/2008 |
| EP | 2308857 | A1 | 4/2011 |
| WO | 2009024541 | A2 | 2/2009 |
| WO | 2012089623 | A1 | 5/2012 |
| WO | 2012089622 | A2 | 7/2012 |
| WO | 2013150052 | A1 | 10/2013 |
| WO | 2016138339 | A1 | 9/2016 |
| WO | 2016164487 | A1 | 10/2016 |
| WO | 2017108954 | A1 | 6/2017 |
| WO | 2017147352 | A1 | 8/2017 |
| WO | 2018039508 | A1 | 3/2018 |
| WO | 2019091936 | A1 | 5/2019 |
| WO | 2019091940 | A1 | 5/2019 |

OTHER PUBLICATIONS

Mashkovsky, M.D., Medicines, M.: Novaya Volna, Aug. 2012, 12+13, 16th Edition, English translation.
Mashkovsky, M.D., Medicines, M.: Novaya Volna, Aug. 2012, 12+13, 16th Edition.
Belikov, V.G., Pharmaceutical Chemistry, Moscow MEDpress-inform, 4th Edition, 27-29, 2007.
Pertsev, I.M. et al., Pharmaceutical and Biomedical Aspects of Drugs, Kharkov Publishing House UkrFA, Chapter 11, 253-254, 1999.
Rohdich, Nadja et al., Field effectiveness and safety of fluralaner plus moxidectin (Bravecto® Plus) against ticks and fleas: a European randomized, blinded, multicenter field study in naturally-infested client-owned cats, Parasites & Vectors, 11:598, Jan. 11, 2018.

*Primary Examiner* — Alton N Pryor
(74) *Attorney, Agent, or Firm* — David J. Kerwick

(57) ABSTRACT

An injectable pharmaceutical composition comprising an isoxazoline compound of Formula (I), or a salt or N-oxide and moxidectin microspheres and a method of preventing or treating a parasite infestation using the same.

Formula (I)

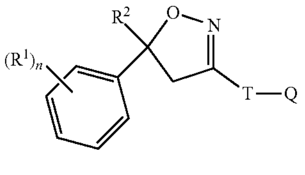

19 Claims, 2 Drawing Sheets

Scanning Electron Micrograph of 10% Moxidectin in Glyceryl Tristearate Microspheres Blood plasma levels of moxidectin and fluralaner (2b) after subcutaneous administration to dogs Blood plasma levels of fluralaner afer subcutaneous administration to dogs

INJECTABLE PHARMACEUTICAL COMPOSITIONS AND USES THEREOF

CROSS-REFERENCE TO RELATED APPLICATIONS

This application is a national stage entry under 35 U.S.C. § 371 of PCT/EP2020/062181 filed May 1, 2020, which claims priority under 35 U.S.C. § 119(e) of provisional application U.S. Ser. No. 62/842,709 filed May 3, 2019, the contents of which are hereby incorporated by reference in their entireties.

BACKGROUND

Isoxazoline compounds are known in the art and these compounds and their use as antiparasitic are described, for example, in US patent application US 2007/0066617, and International Patent applications WO 2005/085216, WO 2007/079162, WO 2009/002809, WO 2009/024541, WO 2009/003075, WO 2010/070068 and WO 2010/079077, the disclosures of which, as well as the references cited herein, are incorporated by reference. This class of compounds is known to possess excellent activity against ectoparasitic arthropods.

WO2015/048371 discloses long acting injectable compositions comprising spirocyclic isoxazoline compounds, one biopolymer and at least one carrier, solvent or excipient.

WO2016/138339 discloses long acting injectable formulations for comprising at least one isoxazoline active agent, a poloxamer and a co-solvent.

WO2016/164487 discloses extended release injectable veterinary formulations comprising at least one isoxazoline active agent, a pharmaceutically acceptable polymer and a solvent for use against parasites.

U.S. Pat. No. 9,609,869 discloses insecticidal compounds based on isoxazoline derivatives for use in controlling pest associated with agriculture, horticulture, animal husbandry and companion animals.

US Patent Application Publication No. 2017/0239218 discloses long acting injectable compositions for combating parasites comprising at least one isoxazoline active agent, a liquid PEG and/or a neutral oil.

Recently another ectoparasitic compound has been described: 2-Chloro-N-(1-cyanocyclopropyl)-5-[1'-methyl-3'-(1,1,2,2,2-pentafluoroethyl)-4'-(trifluoromethyl)[1,5'-bi-1H-pyrazol]-4-yl]benzamide; Tigolaner (CAS RN 1621436-41-6) that was disclosed in WO 2019/012377.

Moxidectin is an active ingredient that is useful for the prevention and treatment of infections and infestations caused by helminths, nematodes, acarids and endo- and ectoparasitic arthropods especially when parenterally administered to animals.

Moxidectin has been disclosed in U.S. Pat. No. 4,916,154. EP0525307 and EP1197207 disclose moxidectin microspheres and injectable compositions and their preparation and use.

An advantageous injectable pharmaceutical composition for veterinary application would be one, that enables a single injection to provide efficacious concentration levels of both active compounds (moxidectin and an isoxazoline compound) in blood plasma of the treated animals over an extended period.

Besides the duration of release for such compositions the technical features of the injectable veterinary formulation, e.g. easiness of application (syringeability and re-suspendability), and the absence of side effects (local injection site reaction and systemic side effects following administration) and the possibility to sterilize the formulation are important features.

It would therefore be desirable to have a technically feasible injectable formulation available that allows the effective and safe release of an effective amount of an isoxazoline compound as described above and moxidectin in a combined formulation over a prolonged time. This would allow the use of these modern compounds under conditions, were separate injections and a repeated administration is not desirable. The composition should also ensure that the excipients do not interfere with the moxidectin microspheres and provide a stable moxidectin content.

Thus, a need exists for an injectable pharmaceutical composition for prolonged release of an isoxazoline compound and moxidectin that overcomes one or more of the limitations of the prior art.

SUMMARY OF THE INVENTION

Accordingly, the present invention provides injectable compositions comprising isoxazoline compounds and moxidectin microspheres with long term efficacy against parasites, safety, physical and chemical stability and reduced risk of injection site irritation.

An embodiment of the invention is an injectable veterinary composition comprising a) moxidectin microspheres comprising from about 50% to about 99% by weight of a fat, wax or mixture thereof, and 0.01-10% by weight of an anti-oxidant; and b) particles of an isoxazoline compound of Formula (I)

Formula (I)

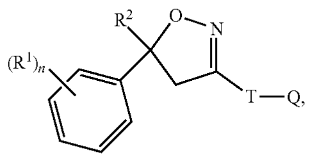

wherein $R^1$=halogen, $CF_3$, $OCF_3$, CN, n=integer from 0 to 3, preferably 1, 2 or 3, $R^2$=$C_1$-$C_3$-haloalkyl, preferably $CF_3$ or $CF_2Cl$, T=5 to 12 membered mono- or bicyclic ring system, which is optionally substituted by one or more radicals Y, Y=methyl, halomethyl, halogen, CN, $NO_2$, $NH_2$—C═S, or two adjacent radicals Y form together a chain, especially a three or four membered chain;

Q=X—$NR^3R^4$ or a 5-membered N-heteroaryl ring, which is optionally substituted by one or more radicals;

X=$CH_2$, $CH(CH_3)$, CH(CN), CO, CS, $R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

R3-1

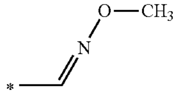

R3-2

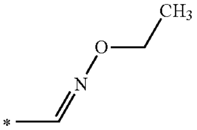

R3-3

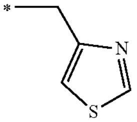

R3-4

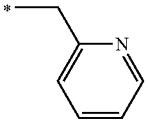

R3-5

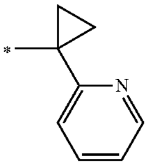

R3-6

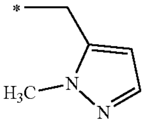

R3-7

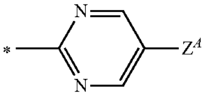

R3-8

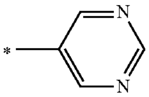

R3-9

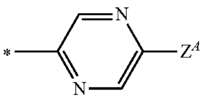

R3-10

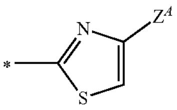

R3-11

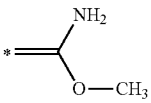

R3-12

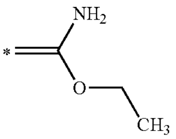

-continued

R3-13

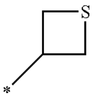

R3-14

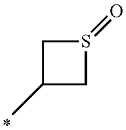

R3-15

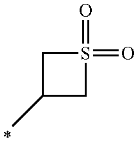

wherein $Z^A$=hydrogen, halogen, cyano, halomethyl ($CF_3$);

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

or $R^3$ and $R^4$ together form a substituent selected from the group consisting of:

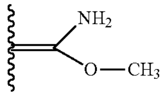 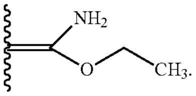

or a salt or solvate thereof;

wherein the moxidectin microspheres and isoxazoline compound particles are suspended in an aqueous carrier comprising one or more suspending agents, one or more wetting agents and/or one or more preservatives, and water.

An additional embodiment is a method of treating or preventing a parasite infestation in an animal comprising administering to an animal in need thereof such injectable veterinary composition.

An additional embodiment is a method of producing such injectable veterinary composition comprising the steps of:

a) Preparing isoxazolines particles, preferably by crystallization;

b) Preparing moxidectin microspheres by melting the fat, wax or mixture thereof and adding the moxidectin and optionally an antioxidant and preparing microspheres, preferably through spinning disk atomization and optionally sieving;

c) filling the moxidectin microspheres obtained by step b) together with the isoxazoline particles obtained by step a) in a first container;

d) preparing the aqueous carrier by dissolving the excipients including suspending agents, wetting agents and/or preservatives in water and filling into a second container;

e) reconstituting the solids by transferring the aqueous carrier from the second container d) to the first container c) and shake to form a ready-to-use suspension.

An additional embodiment is a kit, wherein the kit comprises:

a) a first container comprising a solid mixture of particles of isoxazoline compound of Formula (I) above and moxidectin microspheres as described above;
b) a second container with an aqueous carrier comprising one or more suspending agents, wetting agents and/or preservatives and water; and
c) instructions for reconstituting moxidectin microspheres and isoxazoline compound particles with the aqueous carrier prior to subcutaneous or intramuscular injection to the animal.

An additional embodiment is the method of using such kit to treat or prevent a parasite infestation in an animal by administering the reconstituted suspension by subcutaneous or intramuscular injection to an animal.

DETAILED DESCRIPTION

Figure 1:
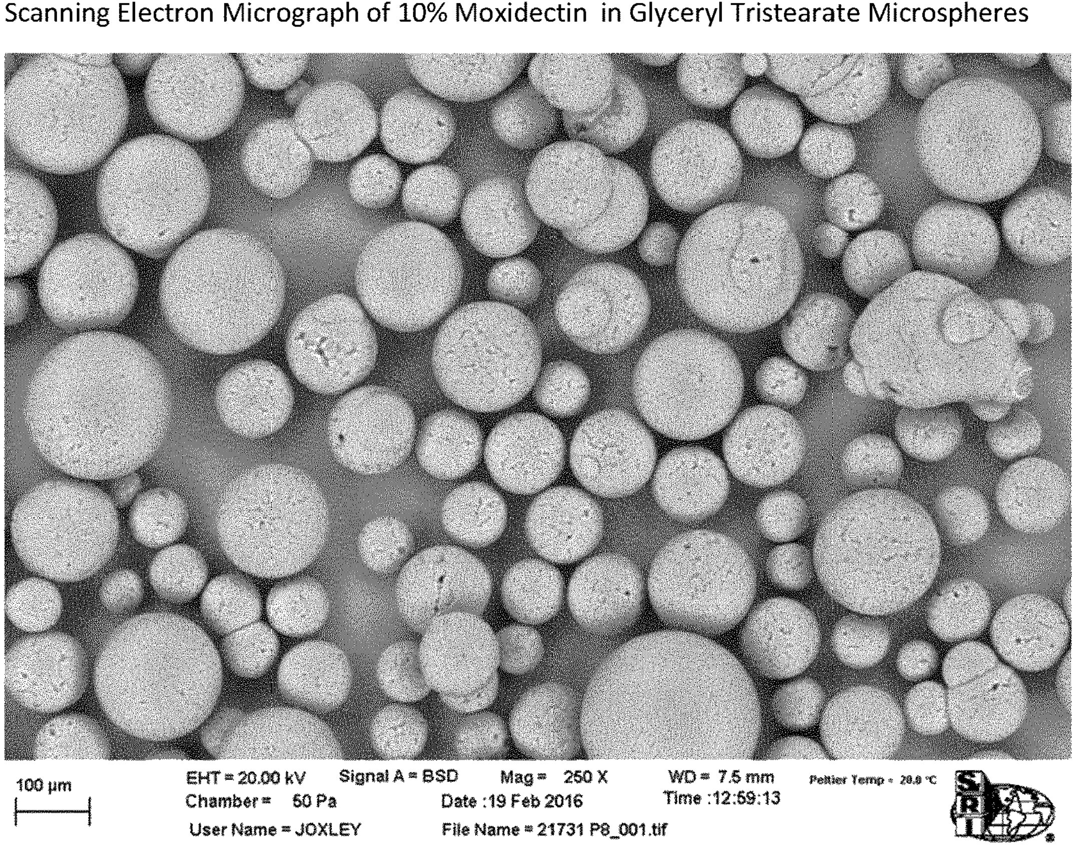
FIG. 1: Scanning Electron Micrograph of 10% Moxidectin in Glyceryl Tristearate Microspheres (GTS)
Figure 2:
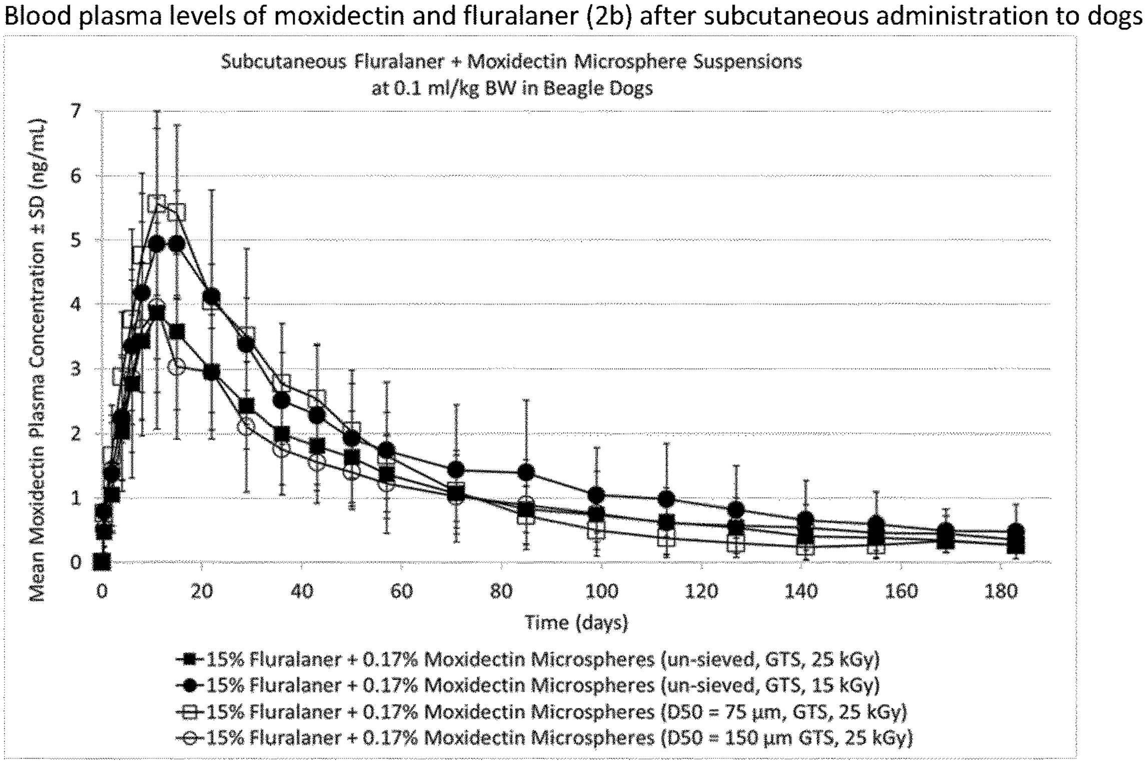
FIGS. 2 and 3: Blood plasma levels of moxidectin (2) and fluralaner (3) after subcutaneous administration to dogs
Figure 3:
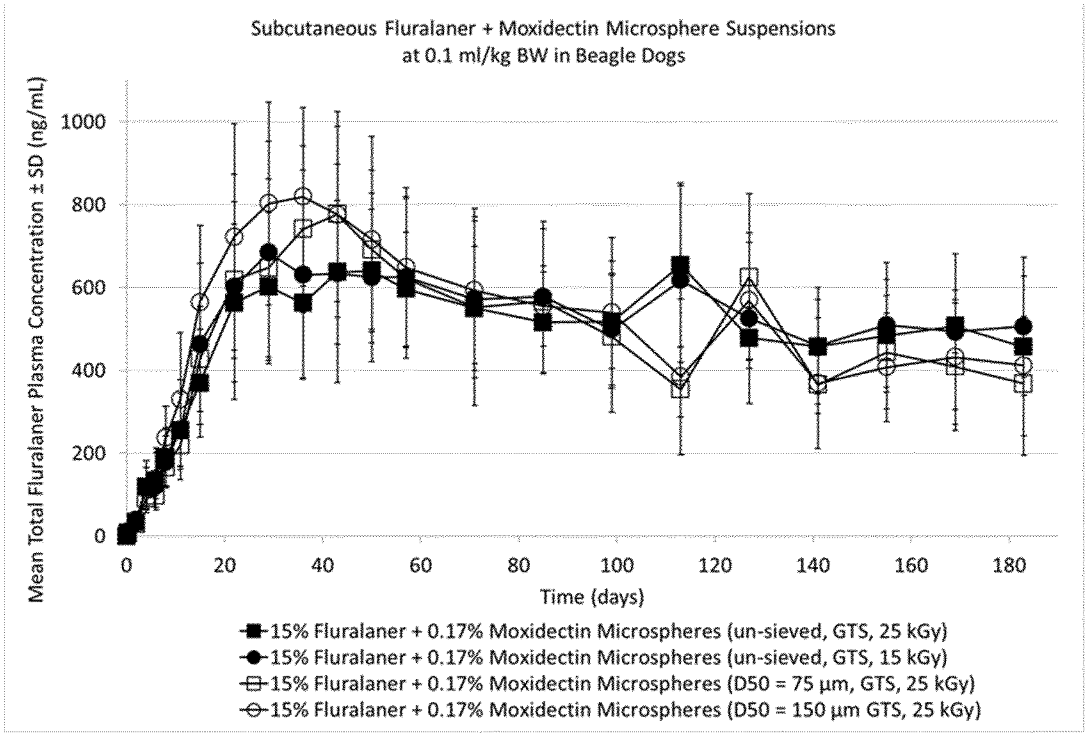

The present invention provides injectable compositions comprising isoxazoline compounds and moxidectin microspheres with long term efficacy against parasites, safety, physical and chemical stability and reduced risk of injection site irritation.

Physical stability of an injectable suspension is especially important to allow correct dosing by injecting a homogeneous suspension comprising the correct amount of both the isoxazoline compound and the moxidectin in one common formulation. The inventors had to overcome the issue that the density of the two different solid components, the isoxazoline (crystalline) particles and the moxidectin microspheres differs—making the provision of a homogeneous suspension difficult. Chemical stability in formulations is especially challenging for moxidectin.

A stable suspension should be formed that can be easily re-suspended with the aqueous caries by gentle shaking without causing foaming or floating or settling of the suspended particles, that would impact the precision of the dosing.

Furthermore, it is important that the final composition to be injected remains physically (and chemically) stable for the whole in-use period after re-suspension/reconstitution.

Additionally, it is advantageous that the injection is safe to the animal after injection and does not cause side effects, especially no unacceptable injection site irritation.

It is further important that the composition can be sterilized by known and accepted procedures, because it will be administered by injection.

The current invention provides such advantageous composition.

Isoxazoline compounds are known in the art and compounds from this class are known to possess excellent activity against parasite infestations, such as ticks and fleas. Embodiments of various isoxazoline compounds for use in the subject invention are provided below.

Injection site irritation is the injury produced at the injection site and surrounding tissue when an animal receives an injection of a pharmaceutical composition. Such injury can be swelling, skin discoloration and tissue necrosis. Though some injection site irritation is inevitable in some animals, injection site swelling of more than 2×2 cm that persists for more than two to three days is generally considered by veterinarians and animal owners to be unacceptable. Minimal injection site irritation means injection site irritation that is less than 2×2 cm that persists for less than two to three days. This standard is generally accepted by veterinarians and their clients in the context of animals receiving injections such as the rabies vaccine.

As used herein, particle size data reported are volume weighted as measured by conventional particle techniques well known to those skilled in the art, such as static light scattering (also known as laser diffraction), image analysis or sieving. More discussion of particle size measurement is provided below.

By syringeable it is meant that the suspension can be withdrawn easily from an ampoule/vial/container into a syringe with a needle and subsequently injected from such a syringe through the needle intramuscularly (im) or subcutaneously (sc) (e.g. 18 gauge).

The particle size of the active ingredient in the suspension can influence the re-suspendability and syringeability i.e. it should be small enough to prevent compaction or caking and to facilitate re-suspension.

Pharmaceutically acceptable excipient is an inert substance that forms a vehicle or medium for a drug product.

A parasite "infestation" refers to the presence of parasites in numbers that pose a risk to humans or animals. The presence can be in the environment, e.g., in animal bedding, on the skin or fur of an animal, etc. When the infestation that is referred to is within an animal, e.g., in the blood or other internal tissues, the term infestation is also intended to be synonymous with the term, "infection," as that term is generally understood in the art, unless otherwise stated.

Aqueous suspension means a composition that comprises particles are mixed with but undissolved in an aqueous liquid comprising water or a water miscible liquid.

Liquid aqueous vehicle is an aqueous carrier or inert medium used as a solvent (or diluent) in which the active agent is formulated and or administered.

Re-constitutable (or resuspendable) formulation is a formulation where a liquid vehicle is one container and one or more active ingredients solids in another container and the content of the two containers are combined to form a liquid solution or suspension final formulation at some point prior to administration to the animal.

Reconstitution is the process of adding a liquid/diluent to a dry ingredient to make a solution or suspension liquid.

The aqueous liquid vehicle contains some excipients for the formulation, for example one or more aqueous diluents, suspending agents one or more wetting agents, one or more preservatives etc.

The pharmaceutical compositions of the invention are of particular value in the control of ectoparasites, i.e. arthropods which are injurious to or spread or act as vectors of diseases in man and livestock and companion animals.

Important arthropod parasites—ectoparasites (insect and acarid pests) are described below in more detail.

Biting insects include, e.g., migrating diperous larvae as *Hypoderma* sp. in cattle, *Gastrophilus* in horses, and *Cuterebra* sp. in rodents, as well as biting flies and mosquitoes spp of all types. For example, bloodsucking adult flies include, e.g., the horn fly or *Haematobia irritans,* the horse fly or *Tabanus* spp., the stable fly or *Stomoxys calcitrans,* the black fly or *Simulium* spp., the deer fly or *Chrysops* spp., the louse fly or *Melophagus ovinus,* the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax,* the cattle grub or *Hypoderma* spp., and the fleeceworm. Mosquitos include, for example, *Culex* spp., *Anopheles* spp., and *Aedes* spp.

Mites include the chicken mite, *Dermanyssus gaffinae;* itch or scab mites or mange mites (*Astigmata*) such as *Sarcoptidae* spp. for example, *Sarcoptes scabiei;* mange mites such as *Psoroptidae* spp. including *Chorioptes bovis, Psoroptes ovis* and *Demodex canis;* the ear mite *Otodectes cynotis;* chiggers e.g., *Trombiculidae* spp. for example the North American chigger, *Trombicula alfreddugesi.*

Ticks include, e.g., soft-bodied ticks including *Argasidae* spp. for example *Argas* spp. and *Ornithodoros* spp.; hard-bodied ticks including *Ixodidae* spp., for example *Ixodes ricinus, Ixodes scapularis, Rhipicephalus sanguineus, Haemaphysalis* spp, *Dermacentor reticulatus, Dermacentor variabilis, Amblyomma americanum* and *Boophilus spp.*

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides fells*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example, *Rhodnius prolixus* and *Triatoma* spp.

The compositions of the invention are of value for the treatment and control of the various lifecycle stages of parasites including egg, nymph, and larvae, juvenile and adult stages.

For the avoidance of doubt, references herein to "treatment" as used herein includes references to curative and palliative treatment, references to "control of ectoparasites" include kill, repel, expel, incapacitate, deter, eliminate, alleviate, minimise, eradicate pests on animals and in the environment of animals.

Prevention is stopping a new or incoming infestation or infection from establishing.

"Control of ectoparasite infestation" means to prevent infestation or to alleviate or reduce parasite numbers in and/or on an animal, and/or to inhibit the development of parasite infestation in or on an animal, in whole or in part.

"Control of endoparasite infestation" means to alleviate or reduce endoparasites, such as nematode and cestode parasites numbers in and/or on an animal, and/or to inhibit the development of parasite infestation in or on an animal, in whole or in part.

Efficacy against endoparasites can be evaluated by counting endoparasites (especially helminthes) directly after necroscopy of the host animal.

The reduction of parasite numbers, especially gastrointestinal helminth parasites can be alternatively measured indirectly by faecal egg or differential larval counts. In this case the effective amount of the composition is determined by the reduction of the number of excreted helminth eggs or larvae in the faeces of the treated animal before and after treatment.

The composition of this invention is administered parenterally via an injection. The concentration of the active ingredients in the composition needs to be sufficient to provide the desired therapeutically or prophylactically effective amount in a volume that is acceptable for injectable administration depending on the animal treated.

The compositions according to this invention are used to treat a helminth infection, such as an infection caused by one or more helminths selected from the group consisting of:

*Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dictyocaulus* spp.; *Dipetalonema* spp; *Dirofilaria* spp.; *Dracunculus* spp.; *Enterobius* spp.; *Filaroides* spp.; *Habronema* spp.; *Haemonchus* spp.; *Heterakis* spp.; *Hyostrongylus* spp.; *Metastrongylus* spp.; *Meullerius* spp. *Necator* spp.; *Nematodirus* spp.; *Nippostrongylus* spp.; *Oesophagostomum* spp.; *Onchocerca* spp.; *Ostertagia* spp.; *Oxyuris* spp.; *Parascaris* spp.; *Stephanurus* spp.; *Strongylus* spp.; *Syngamus* spp.; *Toxocara* spp.; *Strongyloides* spp.; *Teladorsagia* spp.; *Toxascaris* spp.; *Trichinella* spp.; *Trichuris* spp.; *Trichostrongylus* spp.; *Triodontophorous* spp.; *Uncinaria* spp., and/or *Wuchereria* spp.

Another endoparasite which seriously harms animals is *Dirofilaria immitis,* also known as Heartworm. The most common hosts are dogs and cats but other animals such as ferrets and raccoons may also be infected. The parasitic worm is transmitted by the mosquito bites, which carry the heartworm larvae. The adult worms live in the major blood vessels of the lung, causing inflammation of the blood vessels and potentially resulting in heart damage and early death. In advanced infections, the worms enter the heart as well.

In a particularly preferred embodiment of the invention, the compositions of the invention are used to treat or prevent an infection by *Dirofilaria immitis.* In another embodiment the compounds and compositions of the invention are used to treat or prevent an infection by *Dirofilaria repens.*

Control or "Efficacy" of a compound means that the parasite count is reduced, after a first administration, by an amount ranging from 5% to about 100%. The control of arthropods (e.g., insects, acarids) can be insecticidal, and/or acaricidal. The effect of the compounds of the invention can be e.g., ovicidal, larvicidal, nymphicidal and/or adulticidal or a combination thereof.

The effect can manifest itself directly, i.e., killing the parasites either immediately or after some time has elapsed, for example when molting occurs, or by destroying their eggs, or indirectly, e.g., reducing the number of eggs laid and/or the hatching rate.

For an in vivo administration of the compound according to the invention, an effective amount is synonymous with a "pharmaceutically effective amount" which is the dose or amount that treats or ameliorates symptoms and/or signs of parasite infection or infestation by the treated animal or reduces parasite numbers in and/or on an animal, and/or to inhibits the development of parasite infestation in or on an animal, in whole or in part. This latter amount is also readily determined by one of ordinary skill in the art, e.g., by observing or detecting changes in clinical condition or behavior of treated animals, as well as by observing or detecting relative changes in parasite numbers after such treatment.

Systemic administration of medicaments means that the target (organ or parasite) is reached via the bloodstream.

Animal means mammals including companion animals. Companion animal (or pet) means dog, cat or horse, especially dog or cat.

In an embodiment, the isoxazoline compounds for use in the invention also include pharmaceutically acceptable salts, esters, and/or N-oxides thereof. In addition, the reference to an isoxazoline compound refers equally to any of its polymorphic forms or stereoisomers.

In an embodiment, the pharmaceutical composition according to the invention may employ a racemic mixture of an isoxazoline for use in the invention, containing equal amounts of the enantiomers of such isoxazoline compound as described above.

Alternatively, the pharmaceutical composition may use isoxazoline compounds that contain enriched stereoisomers compared to the racemic mixture in one of the enantiomers of the isoxazoline as defined herein.

Also, the pharmaceutical composition may use an essentially pure stereoisomer of such isoxazoline compounds. Such enriched- or purified stereoisomer preparations of an isoxazoline for use in the invention, may be prepared by methods known in the art.

Examples are chemical processes utilizing catalytic asymmetric synthesis, or the separation of diastereomeric salts (see e.g.: WO 2009/063910, and JP 2011/051977, respectively).

Especially preferred is the S-enantiomer.

In an embodiment of an isoxazoline for use in the invention, T is selected from

T-1

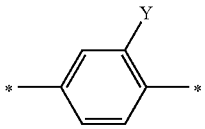

T-2

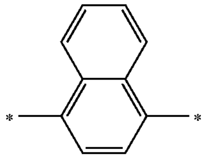

T-3

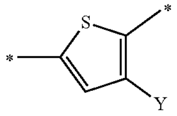

T-4

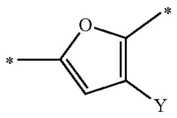

T-5

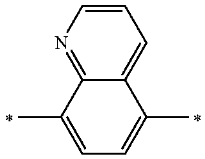

T-6

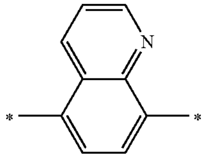

-continued

T-7

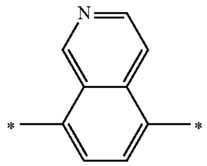

T-8

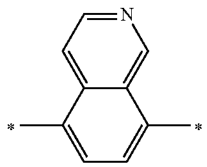

T-9

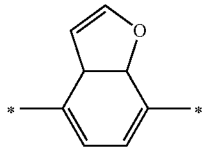

T-10

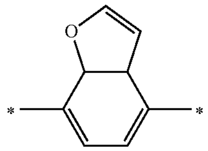

T-11

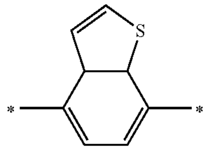

T-12

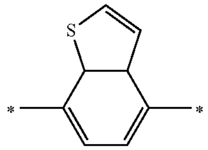

T-13

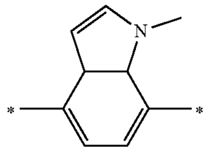

T-14

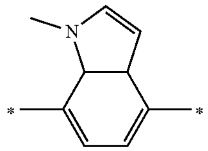

T-15

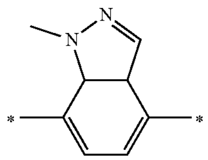

-continued
T-16
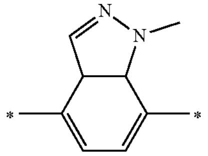
T-17
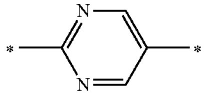
T-18
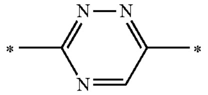
T-19
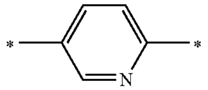
T-20
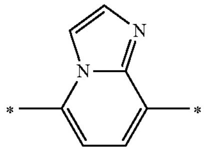
T-21
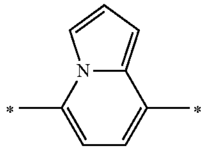
T-22
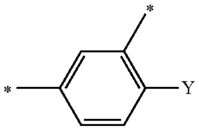
T-23
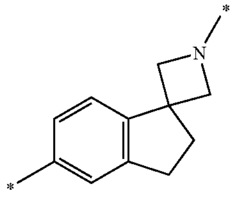
T-24
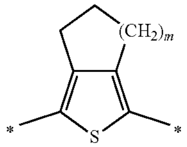
T-25
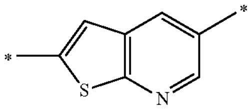
wherein in T-1, T-3 and T-4, the radical Y=hydrogen, halogen, methyl, halomethyl, ethyl, or haloethyl.
In an embodiment of an isoxazoline for use in the invention, Q is selected from
Q-1
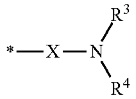
Q-2
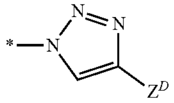
Q-3
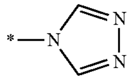
Q-4
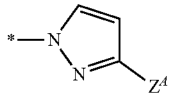
Q-5
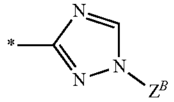
Q-6
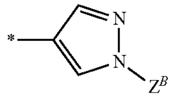
Q-7
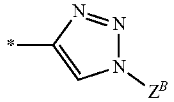
Q-8
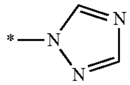
Q-9
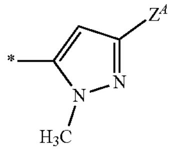
wherein $R^3$, $R^4$, X and $Z^A$ are as defined above, and $Z^B$=
$Z^B$-1
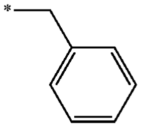
$Z^B$-2
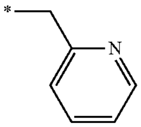
$Z^B$-3
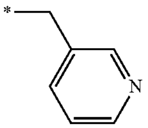

-continued $Z^B$-4

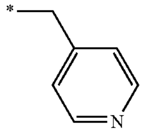

$Z^B$-5

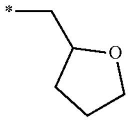

$Z^B$-6

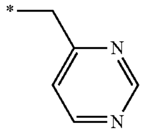

$Z^B$-7

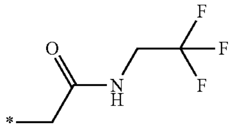

$Z^B$-8

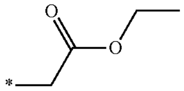

$Z^B$-9

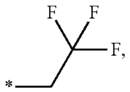

$Z^D$=

$Z^D$-1

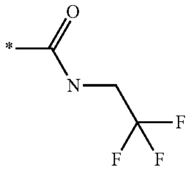

$Z^D$-2

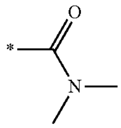

$Z^D$-3

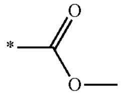

$Z^D$-4

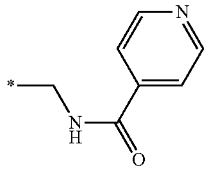

$Z^D$-5

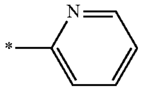

$Z^D$-6

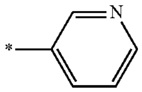

In an embodiment an isoxazoline for use in the invention is as presented in Table 1.

TABLE 1

| $(R^1)_n$ | $R^2$ | $R^3$ | $R^4$ | T | Y | Q | Z | X |
|---|---|---|---|---|---|---|---|---|
| 3-Cl, 5-Cl | $CF_3$ | $CH_2CF_3$ | H | T-2 | — | Q-1 | — | CO |
| 3-Cl, 5-Cl | $CF_3$ | $CH_2CH_3$ | H | T-2 | — | Q-1 | — | CO |
| 3-Cl, 5-Cl | $CF_3$ | $CH_2CH_2OCH_3$ | H | T-2 | — | Q-1 | — | CO |
| 3-Cl, 5-Cl | $CF_3$ | $CH_2C(O)NHCH_2CF_3$ | H | T-2 | — | Q-1 | — | CO |
| 3-Cl, 5-Cl | $CF_3$ | $CH_2C(O)NHCH_2CH_3$ | H | T-2 | — | Q-1 | — | CO |
| 3-$CF_3$, 5-$CF_3$ | $CF_3$ | $CH_2C(O)NHCH_2CF_3$ | H | T-2 | — | Q-1 | — | CO |
| 3-$CF_3$, 5-$CF_3$ | $CF_3$ | $CH_2C(O)NHCH_2CH_3$ | H | T-2 | — | Q-1 | — | CO |
| 3-$CF_3$, 5-Cl | $CF_3$ | $CH_2C(O)NHCH_2CF_3$ | H | T-2 | — | Q-1 | — | CO |
| 3-$CF_3$, 5-Cl | $CF_3$ | $CH_2C(O)NHCH_2CH_3$ | H | T-2 | — | Q-1 | — | CO |
| 3-Cl, 5-Cl | $CF_3$ | — |  | T-2 | — | Q-6 | $Z^B$-7 | CO |
| 3-Cl, 5-Cl | $CF_3$ | — | — | T-2 | — | Q-7 | $Z^B$-7 | CO |
| 3-Cl, 5-Cl | $CF_3$ | — | — | T-2 | — | Q-5 | $Z^B$-7 | CO |
| 3-Cl, 5-Cl | $CF_3$ | — | — | T-2 | — | Q-2 | $Z^D$-1 | CO |
| 3-Cl, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CC$ | H | T-3 | $CH_3$ | Q-1 | — | CO |
| 3-Cl, 5-Cl | $CF_3$ | $CH_2C(O)NHCH_2CN$ | H | T-3 | $CH_3$ | Q-1 | — | CO |
| 3-Cl, 5-Cl | $CF_3$ | $CH_2C(O)NHCH_2CH_3$ | H | T-3 | $CH_3$ | Q-1 | — | CO |
| 3-$CF_3$, 5-$CF_3$ | $CF_3$ | $CH_2C(O)NHCH_2CF_3$ | H | T-3 | $CH_3$ | Q-1 | — | CO |
| 3-$CF_3$, 5-$CF_3$ | $CF_3$ | $CH_2C(O)NHCH_2CH_3$ | H | T-3 | $CH_3$ | Q-1 | — | CO |
| 3-Cl, 4-Cl, 5-Cl | $CF_3$ | $CH_2C(O)NHCH_2CF_3$ | H | T-3 | $CH_3$ | Q-1 | — | CO |
| 3-Cl, 4-Cl, 5-Cl | $CF_3$ | $CH_2C(O)NHCH_2CH_3$ | H | T-3 | $CH_3$ | Q-1 | — | CO |
| 3-Cl, 4-F, 5-Cl | $CF_3$ | $CH_2C(O)NHCH_2CF_3$ | H | T-3 | $CH_3$ | Q-1 | — | CO |
| 3-Cl, 4-F, 5-Cl | $CF_3$ | $CH_2C(O)NHCH_2CH_3$ | H | T-3 | $CH_3$ | Q-1 | — | CO |
| 3-Cl, 5-Cl | $CF_3$ | $CH_2C(O)NHCH_2CF_3$ | H | T-20 | — | Q-1 | — | CO |
| 3-Cl, 5-Cl | $CF_3$ | $CH_2C(O)NHCH_2CH_3$ | H | T-20 | — | Q-1 | — | CO |
| 3-$CF_3$, 5-$CF_3$ | $CF_3$ | $CH_2C(O)NHCH_2CF_3$ | $CH_3$ | T-20 | — | Q-1 | — | CO |
| 3-$CF_3$, 5-$CF_3$ | $CF_3$ | $CH_2C(O)NHCH_2CH_3$ | $CH_3$ | T-20 | — | Q-1 | — | CO |

TABLE 1-continued

| $(R^1)_n$ | $R^2$ | $R^3$ | $R^4$ | T | Y | Q | Z | X |
|---|---|---|---|---|---|---|---|---|
| 3-$CF_3$, 5-$CF_3$ | $CF_3$ | $CH_2C(O)NHCH_2CF_3$ | H | T-20 | — | Q-1 | — | CO |
| 3-$CF_3$, 5-$CF_3$ | $CF_3$ | $CH_2C(O)NHCH_2CH_3$ | H | T-20 | — | Q-1 | — | CO |
| 3-$CF_3$, 5-$CF_3$ | $CF_3$ | $CH_2C(O)NHCH_2CF_3$ | H | T-21 | — | Q-1 | — | CO |
| 3-$CF_3$, 5-$CF_3$ | $CF_3$ | $CH_2C(O)NHCH_2CH_3$ | H | T-21 | — | Q-1 | — | CO |
| 3-Cl, 5-Cl | $CF_3$ | $CH_2C(O)NHCH_2CF_3$ | H | T-21 | — | Q-1 | — | CO |
| 3-Cl, 5-Cl | $CF_3$ | $CH_2C(O)NHCH_2CH_3$ | H | T-21 | — | Q-1 | — | CO |
| 3-Cl, 5-Cl | $CF_3$ | $CH_2CH_2SCH_3$ | H | T-21 | — | Q-1 | — | CO |
| 3-Cl, 4-Cl, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | C(O)-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH_2CH_3$ | H | T-22 | F | Q-1 | — | $CH_2$ |
| 3-Cl, 4-F, 5-Cl | $CF_3$ | $C(O)CH_3$ | H | T-22 | Cl | Q-1 | — | $CH_2$ |
| 3-Cl, 5-Cl | $CF_3$ | $CH_2C(O)NHCH_2CF_3$ | H | T-1 | $CH_3$ | Q-1 | — | CO |
| 3-Cl, 5-Cl | $CF_3$ | $CH_2C(O)NHCH_2CH_3$ | H | T-1 | $CH_3$ | Q-1 | — | CO |
| 3-Cl, 5-Cl | $CF_3$ | $R^3$-1 (Z) | H | T-1 | $CH_3$ | Q-1 | — | CO |
| 3-Cl, 5-Cl | $CF_3$ | $R^3$-1 (E) | H | T-1 | $CH_3$ | Q-1 | — | CO |

In an embodiment an isoxazoline for use in the invention is as presented in Table 2.

TABLE 2

| $(R^1)_n$ | $R^2$ | $R^3$ | $R^4$ | T | Y | Q | Z | X |
|---|---|---|---|---|---|---|---|---|
| 3-Cl, 5-Cl | $CF_3$ | $CH_2CF_3$ | H | T-2 | — | Q-1 | — | CO |
| 3-Cl, 5-Cl | $CF_3$ | $CH_2CH_3$ | H | T-2 | — | Q-1 | — | CO |
| 3-Cl, 5-Cl | $CF_3$ | $CH_2CH_2OCH_3$ | H | T-2 | — | Q-1 | — | CO |
| 3-Cl, 5-Cl | $CF_3$ | $CH_2C(O)NHCH_2CF_3$ | H | T-2 | — | Q-1 | — | CO |
| 3-$CF_3$, 5-$CF_3$ | $CF_3$ | $CH_2C(O)NHCH_2CF_3$ | H | T-2 | — | Q-1 | — | CO |
| 3-$CF_3$, 5-Cl | $CF_3$ | $CH_2C(O)NHCH_2CF_3$ | H | T-2 | — | Q-1 | — | CO |
| 3-Cl, 5-Cl | $CF_3$ | — | | T-2 | — | Q-6 | $Z^B$-7 | |
| 3-Cl, 5-Cl | $CF_3$ | — | — | T-2 | — | Q-7 | $Z^B$-7 | |
| 3-Cl, 5-Cl | $CF_3$ | — | — | T-2 | — | Q-5 | $Z^B$-7 | |
| 3-Cl, 5-Cl | $CF_3$ | — | — | T-2 | — | Q-2 | $Z^D$-1 | |
| 3-Cl, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CC$ | H | T-3 | $CH_3$ | Q-1 | — | CO |
| 3-Cl, 5-Cl | $CF_3$ | $CH_2C(O)NHCH_2CN$ | H | T-3 | $CH_3$ | Q-1 | — | CO |
| 3-$CF_3$, 5-$CF_3$ | $CF_3$ | $CH_2C(O)NHCH_2CF_3$ | H | T-3 | $CH_3$ | Q-1 | — | CO |
| 3-Cl, 4-Cl, 5-Cl | $CF_3$ | $CH_2C(O)NHCH_2CF_3$ | H | T-3 | $CH_3$ | Q-1 | — | CO |
| 3-Cl, 4-F, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CF_3$ | H | T-20 | — | Q-1 | — | CO |
| 3-$CF_3$, 5-$CF_3$ | $CF_3$ | $CH_2C(O)NHCH_2CF_3$ | $CH_3$ | T-20 | — | Q-1 | — | CO |
| 3-$CF_3$, 5-$CF_3$ | $CF_3$ | $CH_2C(O)NHCH_2CF_3$ | H | T-20 | — | Q-1 | — | CO |
| 3-$CF_3$, 5-$CF_3$ | $CF_3$ | $CH_2C(O)NHCH_2CF_3$ | H | T-21 | — | Q-1 | — | CO |
| 3-Cl, 5-Cl | $CF_3$ | $CH_2C(O)NHCH_2CF_3$ | H | T-21 | — | Q-1 | — | CO |
| 3-Cl, 5-Cl | $CF_3$ | $CH_2CH_2SCH_3$ | H | T-21 | — | Q-1 | — | CO |
| 3-Cl, 4-Cl, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | C(O)-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH_2CH_3$ | H | T-22 | F | Q-1 | — | $CH_2$ |
| 3-Cl, 4-F, 5-Cl | $CF_3$ | $C(O)CH_3$ | H | T-22 | Cl | Q-1 | — | $CH_2$ |
| 3-Cl, 5-Cl | $CF_3$ | $CH_2C(O)NHCH_2CF_3$ | H | T-1 | $CH_3$ | Q-1 | — | CO |
| 3-Cl, 5-Cl | $CF_3$ | $R^3$-1 (Z) | H | T-1 | $CH_3$ | Q-1 | — | CO |
| 3-Cl, 5-Cl | $CF_3$ | $R^3$-1 (E) | H | T-1 | $CH_3$ | Q-1 | — | CO |

In an embodiment an isoxazoline for use in the invention is the compound:

(Formula 2)

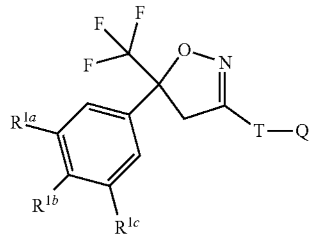

wherein $R^{1a}$, $R^{1b}$, $R^{1c}$ are independently from each other: hydrogen, Cl or $CF_3$.

Preferably $R^{1a}$ and $R^{1c}$ are Cl or $CF_3$, and $R^{1b}$ is hydrogen, T is

T-1

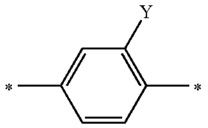

T-2

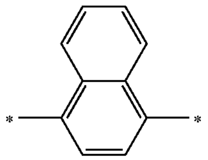

T-3

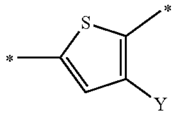

T-20

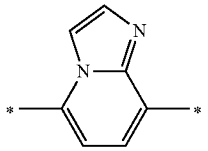

T-21

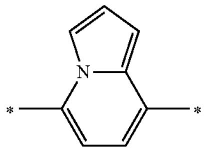

T-23

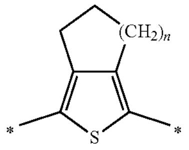

T-24

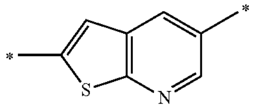

wherein Y is methyl, bromine, Cl, F, CN or $C(S)NH_2$; n=1 or 2; and Q is as described above.

In an embodiment of an isoxazoline as defined herein, $R^3$ is H, and $R^4$ is: $-CH_2-C(O)-NH-CH_2-CF_3$, $-CH_2-C(O)-NH-CH_2-CH_3$, $-CH_2-CH_2-CF_3$ or $-CH_2-CF_3$.

In an embodiment of the pharmaceutical composition according to the invention, the isoxazoline is one or more selected from the group consisting of fluralaner, afoxolaner, lotilaner or sarolaner. In another embodiment of the pharmaceutical composition according to the invention, the isoxazoline compound is one or more selected from the group consisting of fluralaner, afoxolaner, tigolaner, lotilaner or sarolaner.

In one embodiment the compound of Formula (I) is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN 864731-61-3-USAN fluralaner).

In another embodiment the compound of Formula (I) is 4-[5-[3-Chloro-5-(trifluoromethyl)phenyl]-4,5-dihydro-5-(trifluoromethyl)-3-isoxazolyl]-N-[2-oxo-2-[(2,2,2-trifluoroethyDamino]ethyl]-1-naphthalenecarboxamide (CAS RN 1093861-60-9, USAN-afoxolaner) that was disclosed in WO2007/079162-.

In an embodiment of the pharmaceutical composition according to the invention the isoxazoline is lotilaner (CAS RN: 1369852-71-0; 3-methyl-N-[2-oxo-2-(2,2,2-trifluoroethylamino)ethyl]-5-[(5S)-5-(3,4,5-trichlorophenyl)-5-(trifluoromethyl)-4H-1,2-oxazol-3-yl]thiophene-2-carboxamide).

In an embodiment of the pharmaceutical composition according to the invention the isoxazoline is sarolaner (CAS RN: 1398609-39-6; 1-(5'-((5S)-5-(3,5-dichloro-4-fluorophenyl)-5-(trifluoromethyl)-4,5-dihydroisoxazol-3-yl)-3'-H-spiro(azetidine-3,1'-(2) benzofuran)-1-yl)-2-(methylsulfonyl) ethanone).

In another embodiment the compound of Formula (I) is (Z)-4-[5-(3,5-Dichlorophenyl)-5-trifluoromethyl-4,5-dihydroisoxazol-3-yl]-N-[(methoxyimino)methyl]-2-methylbenzamide (CAS RN 928789-76-8).

In another embodiment the compound of Formula (I) is 4-[5-(3,5-dichlorophenyl)-5-(trifluoromethyl)-4H-isoxazol-3-yl]-2-methyl-N-(thietan-3-yl)benzamide (CAS RN 1164267-94-0) that was disclosed in WO2009/0080250.

In another embodiment the compound of Formula (I) is 4-[5-[3-Chloro-5-(trifluoromethyl)phenyl]-4,5-dihydro-5-(trifluoromethyl)-3-isoxazolyl]-N-[2-oxo-2-[(2,2,2-trifluoroethyDamino]ethyl]-1-naphthalenecarboxamide (CAS RN 1093861-60-9, USAN-afoxolaner) that was disclosed in WO2007/079162-.

In another embodiment the compound of Formula (I) is 5-[5-(3,5-Dichlorophenyl)-4,5-dihydro-5-(trifluoromethyl)-3-isoxazolyl]-3-methyl-N-[2-oxo-2-[(2,2,2-trifluoroethyDamino]ethyl]-2-thiophenecarboxamide (CAS RN 1231754-09-8) that was disclosed in WO2010/070068.

In an alternative embodiment the isoxazoline compound is 2-Chloro-N-(1-cyanocyclopropyl)-5-[1'-methyl-3'-(1,1,2,2,2-pentafluoroethyl)-4'-(trifluoromethyl)[1,5'-bi-1H-pyrazol]-4-yl]benzamide; Tigolaner (CAS RN 1621436-41-6) that was disclosed in WO 2019/012377.

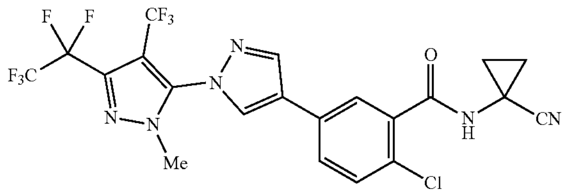

$C_{21}H_{13}ClF_8N_6O$ 1621436-41-6

The isoxazoline compounds may exist in various isomeric forms. A reference to a compound for use in this invention always includes all possible isomeric forms of such compound.

In one embodiment the racemic form of the isoxazoline compound is present in the composition according to the invention. In another embodiment the S-enantiomer is present.

In a specific preferred embodiment, the S-enantiomer of fluralaner is present.

In another preferred embodiment the isoxazoline compound according to Formula (I) is the (S)-enantiomer of afoxolaner (also referred to as esafoxolaner)

One important aspect of the present invention is the combination of isoxazoline compound particles with stable microspheres comprise moxidectin, dissolved in a fat, a wax or a mixture thereof having a melting point above about 40° C., and preferably above about 50° C. in an aqueous suspension.

These moxidectin microsphere may be sterilized by gamma radiation or electron beam without significant degradation.

Microspheres are Small Spherical Particles with Diameter From 1-1000 μm, Made Up of Polymeric Waxy or Other Protective Material Preferred stable moxidectin microspheres for use in the injectable formulation according to the invention comprise on a weight basis about 75% to 95% by weight of a fat, a wax or a mixture thereof. Preferably the microspheres comprise about 1 to 25% of moxidectin and about 0.01-1% of an antioxidant.

In one alternative embodiment, the compositions comprise microspheres as described herein of a different macrocyclic lactone compound including, but not limited to, avermectins or milbemycins. In some embodiments, such avermectin or milbemycin is eprinomectin, abamectin, ivermectin, selamectin, milbemectin, milbemycin D, or milbemycin oxime.

In one embodiment the composition comprises a combination of fluralaner with eprinomectin, or fluralaner with milbemycin oxime, selamectin or moxidectin.

In one embodiment the composition comprises a combination of afoxolaner with eprinomectin, or afoxolaner with milbemycin oxime, selamectin or moxidectin.

In one embodiment the composition comprises a combination of sarolaner with eprinomectin, or sarolaner with milbemycin oxime, selamectin or moxidectin.

In one embodiment the composition comprises a combination of lotilaner with eprinomectin, or lotilaner with milbemycin oxime, selamectin or milbemycin oxime, selamectin or moxidectin.

Injectable compositions generally need to be sterilized prior to administration to an animal. Gamma radiation or electron beam irradiation are effective sterilization processes for eliminating microbial contaminants.

However, Moxidectin readily degrades and lose much of its biological activity when irradiated. This destructive and degradative response to irradiation precludes the use of gamma radiation or election beam as a means to sterilize certain moxidectin-containing compositions.

The moxidectin microspheres can be irradiation sterilized for injection as shown in Example 2 without negatively impacting the stability of the active ingredients. The moxidectin microspheres comprise or consist essentially of, on a weight basis, about 50% to 99% by weight of a fat, a wax or a mixture thereof having a melting point above about 40° C., about 1% to 50% of moxidectin, and about 0.01-10% of an anti-oxidant.

The injectable pharmaceutical composition achieves an effective extended release effect of moxidectin and the isoxazoline compound.

The invention also provides a method for introducing and maintaining blood levels of an moxidectin and an isoxazoline compound, especially of moxidectin and fluralaner in animals for an extended period of time; and a method for the prevention or treatment of infections and infestations caused by helminths, nematodes, acarids and endo- and ectoparasitic arthropods in animals.

In an embodiment, the moxidectin is present in the injectable veterinary composition an amount between about 0.01% by weight to about 1.0% by weight.

In a specific embodiment the injectable composition of the invention comprises 15% fluralaner and 0.17% moxidectin.

Waxes and fats which are suitable in the compositions of this invention generally have melting points higher than 40° C., preferably higher than 50° C.

The term "wax" as used herein is defined as set forth in Hawley's The Condensed Chemical Dictionary, Eleventh Edition, as a low-melting organic mixture or compound of high molecular weight, solid at room temperature and generally similar in composition to fats and oils except that it contains no glycerides.

Some are hydrocarbons; others are esters of fatty acids and alcohols. These compounds include saturated or unsaturated long chain $C_{10}$-$C_{24}$ fatty adds, alcohols, esters, salts, ethers or mixtures thereof. They are classed among the lipids. Waxes are thermoplastic, but since they are not high polymers, they are not considered in the family of plastics.

Common properties of these waxes include water repellency; smooth texture; nontoxicity; and freedom from objectionable odor and color. They are combustible and have good dielectric properties. They are soluble in most organic solvents and are insoluble in water. The major types are as follows:

A. Natural
1. Animal (beeswax, lanolin, shellac wax, Chinese insect wax)
2. Vegetable (camauba, candelilla, bayberry, sugar cane)

B. Mineral
1.Fossil or earth waxes (ozocerite, ceresin, montan)
2. petroleum waxes (paraffin, microcrystalline) (slack or scale wax)

D. Synthetic
1. Ethylenic polymers and polyol ether-esters ("Carbowax")
2. Chlorinated naphthalenes ("Halowax").

The term "fat" as used herein is defined as as a glyceryl ester of higher fatty acids such as stearic and palmitic. Such esters and their mixtures are solids at room temperatures and exhibit crystalline structure. Lard and tallow are examples.

The term "fat" usually refers to triglycerides specifically, whereas "lipid" is all-inclusive.

The fat is preferably composed of triglyceryl esters of long chain C12-C22 fatty acids, such as stearates, palmitates, laurates, myristates, arachidates and behenates, and mixtures thereof; those having melting points greater than 50° C. are most preferred.

Glyceryl tristearate is a most preferred fat in the practice of this invention.

An anti-oxidant suitable in the practice of this invention includes any of the antioxidants known in the art as suitable for stabilizing the moxidectin compound.

The antioxidant of the invention may be defined as an organic compound added to rubber, natural fats and oils, food products, gasoline, and lubricating oils to retard oxidation, deterioration, rancidity, and gum formation, respectively. Rubber antioxidants are commonly of an aromatic amine type, such as di-,8-naphthyl-p-phenylene-diamine and phenyl-,8-naphthylamine.

Many antioxidants are substituted phenolic compounds (butylated hydroxyanisole, di-tertbutyl-p-cresol, and propyl gallate). Food antioxidants are effective in very low concentration and not only retard rancidity but protect the nutritional value by minimizing the breakdown of vitamins and essential fatty acids.

The present moxidectin microspheres can be sterilized with gamma radiation or electron beam and maintain shelf life without significant loss of biological activity. Moxidectin generally easily degrades and loses much of its biological activity, especially when irradiated.

Antioxidants suitable for use in the microsphere compositions of the invention include tocopherol, ascorbic acid, ascrobyl palmitate, fumaric acid, malic acid, sodium ascorbate, sodium metabisulfate, n-propyl gallate, BHA (butylated hydroxy anisole), BHT (butylated hydroxy toluene) monothioglycerol, tert-butylhydroxy quinone, 6-ethoxy-1,2-dihydro-2,2,4-trimethylquinoline and the like with butylated hydroxytoluene being a preferred antioxidant. In certain embodiments, the antioxidants are generally added to the formulation in amounts of from about 0.01 to about 2.0%, based upon total weight of the formulation, with about 0.05 to about 1.0% being especially preferred.

The microsphere compositions of the invention may be sterilized with gamma radiation or electron beam and maintain shelf life without significant loss of biological activity.

The microspheres for use in the composition of the invention may be prepared by incorporating the moxidectin, antioxidant and optionally other excipients with a molten fat, wax or mixture thereof and then forming microspheres of the resulting mixture by a variety of techniques such as emulsifying or atomizing the mixture or by processing the mixture of ingredients and molten fat, wax or mixture thereof mechanically and cooling, for example utilizing a centrifugal disc.

Alternatively, the mixture of active ingredients, antioxidants, excipients and fat, waxes and mixtures thereof and oil, may be cooled to give a solid which may then be processed by procedures such as milling, grinding and the like.

The stable microspheres of the invention are dispersed in a pharmaceutically and pharmacologically acceptable aqueous solution to obtain a slow release composition for parenteral administration.

Excipients such as surfactants, salts, buffers or mixtures thereof may be included in the vehicle of the invention.

The amounts of said excipients suitable for use in the invention range from about 0.1% to 20% on a weight basis.

Preferably, a cellulose derivative such as carboxymethylcellulose comprises about 1-5% by weight and an inorganic salt, e.g., NaCl, comprises about 0.1-2% by weight of the vehicle.

Maintained blood levels of the active compounds are associated with the protection or treatment of warm-blooded animals against infections and infestation by helminths, nematodes, acarids and endo- and ectoparasitic arthropods.

Maintaining the blood levels is an indication of the slow release of the active ingredient.

The invention includes the use of the compositions herein to introduce and maintain levels of moxidectin and isoxazoline compounds, especially fluralaner in the blood stream of animals.

It has been found that the inventive injectable compositions comprising particles of isoxazoline compounds and moxidectin microspheres with a defined particle size show desirable bioavailability and duration of efficacy, while causing minimal irritation at the injection site.

The compositions also provide desirable safety profiles toward the warm-blooded and bird animal recipients.

In addition, it has been discovered that a single administration of such compositions generally provides potent activity against one or more parasites (e.g., ectoparasites, e.g. fleas, ticks or mites), while also tending to provide fast onset of activity, long duration of activity, and/or desirable safety profiles.

The invention also provides methods for the treatment or prevention of parasitic infections and infestations in animals, comprising administering an effective amount of injectable compositions comprising an antiparasitic effective amount of at least one isoxazoline compound and moxidectin microspheres of a defined particle size together with a pharmaceutically acceptable excipient.

Surprisingly, it has been found that the inventive compositions described herein exhibit superior broad-spectrum efficacy against harmful parasites (e.g. ectoparasites such as fleas and ticks) more rapidly, and over a long duration compared to other injectable compositions known in the art while exhibiting minimal irritation at the injection site.

The pharmaceutical composition of the current invention can be administered by subcutaneous or intramuscular injection.

The long-acting injectable compositions of the invention include pharmaceutically acceptable excipients.

Pharmaceutically acceptable excipients include, but are not limited to, surfactants, antioxidants, preservatives, pH stabilizing agents (e.g. buffers), and other non-active excipients.

In another embodiment, the compositions of the invention may comprise about 0.01% to about 20% (w/v) of pharmaceutically acceptable excipients.

In other embodiments, the compositions may comprise about 0.01% to about 5% (w/v), about 0.1% to about 10% (w/v) or about 0.1% to about 5% (w/v) of pharmaceutically acceptable excipients. In other embodiments the compositions may comprise about 5 to about 15% (w/v) or about 5 to about 10% (w/v) of pharmaceutically acceptable excipients.

In yet another embodiment, the compositions may comprise about 7 to about 10% of pharmaceutically acceptable excipients.

Surfactants may be present in the inventive compositions at concentrations of about 0.1% to about 10% (w/w), about 1% to about 10% (w/w) or about 5% to about 10% (w/w). More typically, surfactants may be present at concentrations of about 0.1% to about 5% (w/w) or about 1 to about 5% (w/w).

Examples of surfactants that may be used in the compositions include, but are not limited to, glyceryl monooleate, polyoxyethylene sorbitan fatty acid esters, sorbitan esters including sorbitan monooleate (Span® 20), polyvinyl alcohol, polysorbates including polysorbate 20 and polysorbate 80, d-a-tocopherol polyethylene glycol 1000 succinate (TPGS), sodium lauryl sulfate, co-polymers of ethylene oxide and propylene oxide (e.g. poloxamers such as LUTROL® F87 and the like), polyethylene glycol castor oil derivatives including polyoxyl 35 castor oil (Cremophor® EL), polyoxyl 40 hydrogenated castor oil (Cremophor® RH 40), polyoxyl 60 hydrogenated castor oil (Cremophor® RH60); propylene glycol monolaurate (LAUROGLYCOL®); glyceride esters including glycerol caprylate/caprate (CAPMUL® MCM), polyglycolized glycerides) (GELUCIRE®, PEG 300 caprylic/capric glycerides (Softigen® 767), PEG 400 caprylic/capric glycerides (Labrasol®), PEG 300 oleic glycerides (Labrafil® M-1944CS), PEG 300 linoleic glycerides (Labrafil® M-2125CS); polyethylene glycol stearates and polyethylene glycol hydroxy stearates including polyoxyl 8 stearate (PEG 400 monostearate), polyoxyl 40 stearate (PEG 1750 monostearate, and the like).

Polyethylene glycol stearates (synonyms include macrogol stearates, polyoxylstearates, polyoxyethylene stearates, ethoxylated stearates; CAS No. 9004-99-3, 9005-08-7) are mixtures of mono- and distearate esters of mixed polyoxyethylene polymers. Polyethylene glycol hydroxystearate is a mixture of mono- and diesters of hydroxystearic acid with polyethylene glycols. One polyethylene glycol hydroxystearate that may be used in the compositions is polyethylene glycol 12-hydroxystearate. In another embodiment, the inventive compositions may include the surfactant polyethylene glycol 15 12-hydroxystearate (Kolliphor® HS 15 from BASF), a mixture of mono- and diesters of 12-hydroxystearic acid with 15 moles of ethylene oxide.

Again, these compounds, as well as their amounts are well known in the art.

In another embodiment of the invention, the inventive compositions may include polyoxyl 35 castor oil (Kolliphor® EL) as a surfactant. In other embodiments, the inventive compositions may include polyoxyl 40 hydrogenated castor oil (Kolliphor® RH 40) or polyoxyl 60 hydrogenated castor oil as surfactants. The compositions of the invention may also include a combination of surfactants.

The inventive compositions may contain other inert ingredients such as antioxidants, preservatives, or pH stabilizers. These compounds are well known in the composition art.

Antioxidants such as vitamin E, alpha tocopherol, ascorbic acid, ascorbyl palmitate, citric acid, fumaric acid, malic acid, sodium ascorbate, sodium metabisulfate, sodium metabisulfite, n-propyl gallate, BHA (butylated hydroxy anisole), BHT (butylated hydroxy toluene), BHA and citric acid, monothioglycerol, tert-butyl hydroquinone (TBHQ), benzyl alcohol and the like, may be added to the present composition.

The antioxidants are generally included in the compositions of the invention in amounts of about 0.01% to about 3%, or from about 0.01 to about 2% (w/v), based upon total weight of the composition (w/w). In another embodiment, the compositions contain about 0.05 to about 1.0% (w/w) of one or a mixture of antioxidants.

Preservatives, such as benzyl alcohol, are suitably used in the composition in amounts ranging from about 0.01 to about 10.0%, with about 0.05 to about 5.0% being especially preferred. Other preservatives include parabens (methylparaben and/or propylparaben), benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like.

Preferred ranges for these compounds include from about 0.01 to about 5%.

Preferred is benzyl alcohol.

Compounds which stabilize the pH of the composition may also be present. Again, such compounds are well known to a practitioner in the art as well as how to use these compounds. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycimate, tris, glutamic acid/glutamates and sodium carbonate, especially sodium phosphate or sodium citrate.

Aqueous suspensions may comprise the isoxazoline compound particles and moxidectin microspheres as described herein in admixture with excipients suitable for the manufacture of aqueous suspensions.

Such excipients include suspending agents, for example, sodium carboxymethylcellulose, methylcellulose, hydroxypropylmethylcellulose, sodium alginate, polvinylpyrrolidone, gum tragacanth and gum acacia; dispersing or wetting agents include naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate.

The aqueous suspensions may also contain one or more preservatives, for example ethyl, or n-propyl, p-hydroxybenzoate.

Dispersible powders and granules suitable for preparation of an aqueous suspension by the addition of water may provide the isoxazoline compound and moxidectin microspheres in admixture with a dispersing or wetting agent, suspending agent and one or more preservatives. Suitable dispersing or wetting agents and suspending agents are exemplified by those already mentioned above.

In one embodiment the isoxazoline compound is suspended in an aqueous suspension wherein the liquid carrier (diluent) is water.

In another embodiment the liquid carrier (diluent) of the aqueous suspension comprises water and a co-solvent.

Co-solvents that might be used in the inventive injectable compositions comprising a isoxazoline compound and moxidectin microspheres may be a single or a blend of co-solvents.

In one embodiment, the co-solvents used in the aqueous injectable compositions of the present invention include polar solvents that are miscible in water.

Non-limiting examples of these co-solvents include ethanol, isopropanol, benzyl alcohol, glycol ethers (e.g., including, but limited to diethyleneglycol monoethyl ether (DGME, Transcutol®, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), liquid polyethylene glycols (PEGs) (for example, PEG 400), propylene glycol, carbonates (e.g., propylene carbonate), 2-pyrrolidone, N-methylpyrrolidone, dimethyl isosorbide (DMI), dimethylacetamide, dimethylsulfoxide, glycerol formal or a mixture of at least two of these solvents.

In one embodiment, the compositions of the invention comprise a polar protic solvent including, but not limited to, an alcohol such as ethanol, isopropanol or a glycol or glycol ether. In another embodiment, the long-acting injectable compositions of the invention comprise a polar aprotic solvent such as N-methylpyrrolidone, dimethyl isosorbide, dimethylacetamide, dimethylsulfoxide or propylene carbonate.

In an embodiment, the isoxazoline compounds may exist in various isomeric forms. A reference to an isoxazoline compound always includes all possible isomeric forms of such compound.

Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound.

Especially preferred is the (S) enantiomer. In some embodiments, the compound is a non-chiral compound.

In an embodiment, the isoxazoline compounds of Formula (I) can be prepared according to one or other of the processes described e.g. in Patent Applications US 2007/0066617, WO 2007/079162, WO 2009/002809, WO 2009/080250, WO 2010/070068, WO 2010/079077, 2011/075591 and WO 2011/124998 or any other process coming within the competence of a person skilled in the art who is an expert in chemical synthesis.

For the chemical preparation of the products of the invention, a person skilled in the art is regarded as having at his disposal, inter alia, the entire contents of "Chemical Abstracts" and of the documents which are cited therein.

In an embodiment, the isoxazoline compound is in suspension in the composition. In an embodiment, the suspension is aqueous. In an alternative embodiment, the suspension is non-aqueous.

In an embodiment, the pharmaceutical composition is substantially organic solvent free.

In an embodiment, the pharmaceutical composition comprises a surfactant/wetting agent. In another embodiment, the surfactant/wetting agent is poloxamer.

Alternatives to the poloxamer are other water soluble/miscible non-ionic surfactants including sorbitan fatty acid esters (Spans), polyoxyethylene sorbitan fatty acid esters (polysorbates/Tweens), polyoxyethylene castor oil derivatives (Cremaphors), polyoxyethylene stearates, lecithin and TPGS (d-α-Tocopheryl polyethylene glycol 1000 succinate).

The surfactant/wetting agent is present in the composition in an amount of about 0.01% w/v to about 0.5% w/v or about 0.05% w/v to about 0.1% w/v.

Poloxamers are nonionic triblock copolymers composed of a central hydrophobic chain of polyoxypropylene (poly(propylene oxide)) flanked by two hydrophilic chains of polyoxyethylene (poly(ethylene oxide)) (see U.S. Pat. No. 3,740,421).

Poloxamer 124 is poly(ethylene glycol)-block-poly(propylene glycol)-block-poly(ethylene glycol, CAS Number 9003-11-6. Also known as Lutrol L44 or Kollisolv P124.

Lutrol F68 is another poly(ethylene glycol)-block-poly(propylene glycol)-block-poly(ethylene glycol), Also known as Poloxamer 188 or Kolliphor P188.

In an embodiment, the pharmaceutical composition comprises a suspending agent. In an embodiment, the suspending agent is carboxy methyl cellulose, especially sodium carboxy methyl cellulose (NaCMC).

In an alternative embodiment, the suspending agent is methylcellulose or polyvinyl pyrrolidone.

In an embodiment, the pharmaceutical composition comprises a preservative. In an embodiment, the preservative is benzyl alcohol.

In an alternative embodiment, the preservative is m-cresol, benzalkonium chloride, methylparaben, or propylparaben.

The injectable pharmaceutical compositions may be made by combining and mixing the solid components and then suspending the solid mixture in the diluent.

The method of preparing the injectable pharmaceutical composition comprising combining isoxazoline particles with the moxidectin microspheres to form a solid mixture, which is in a later step reconstituted with an aqueous liquid carrier to form an aqueous suspension ready for injection.

In an embodiment, the aqueous liquid carrier is water.

In an alternative embodiment, the diluent is an oil or a solvent with little or no solubility for the isoxazoline compound and the moxidectin microsphere components.

The pharmaceutical composition further comprises a surfactant/wetting agent.

Specific surfactants/wetting agents and alternatives for the surfactant/wetting agent are discussed in this specification and in the Examples.

The pharmaceutical composition further comprises additional excipients such as a suspending agent, or a preservative.

Specific examples of suitable excipients and alternatives agent are discussed in this specification below and in the Examples.

Isoxazoline Compound Particle and Moxidectin Microsphere Particle Size and Measurement It has been found that the inventive injectable compositions comprising particles of isoxazoline compounds with a defined particle size have especially beneficial properties.

In one embodiment the moxidectin microspheres and isoxazoline compound particles are of the same particle size.

Therefore, in this specification the reference to "isoxazoline compound particle size includes reference to compositions in which the moxidectin microspheres are of the same particle size and are measured by the same methods.

In an embodiment, the isoxazoline compound and/or moxidectin microsphere has a particle size distribution of D50 as measured by a static light scattering instrument of from about 25 microns to about 250 microns, particle size of from about 11 microns to about 250 microns, particle size of from about 50 microns to about 150 microns, particle size of from about 75 microns to about 130 microns, particle size of from about 90 microns to about 110 microns. particle size of from about 30 microns to about 100 microns.

Particle size distribution describes the relative amount of particles present according to size. D10 is a particle size distribution that expresses the size that 10% of the particles are smaller than.

D50 is a particle size measurement distribution that expresses the size that 50% of the particles are smaller than.

D90 is a particle size measurement distribution that expresses the size that 90% of the particles are smaller than.

In another embodiment the particle size is different.

In one embodiment the particle size of the isoxazoline compound and the moxidectin microsphere is in a similar range.

In another embodiment the particle size is not in a similar range.

In a particular embodiment, the D10 of the isoxazoline compound particle size is greater than 10 μm, the D50 of the particle size is 80 to 120 μm, and the D90 of the particle size less than 210 μm.

In a particular embodiment, for moxidectin microspheres the D10 of the particle size is greater than 50 μm, the D50 of the particle size is 100 to 150 μm, and the D90 of the particle size is less than 200 μm.

In a particular embodiment, the D10 of particle size is about 10 μm, about 20 μm, about 30 μm, about 40 μm, about 50 μm, about 60 μm, or about 80 μm.

In a particular embodiment, the D10 of particle size of the moxidectin microspheres is about 80 μm.

In a particular embodiment, the D50 of particle size is about 50 µm, about 75 µm, about 80 µm, about 90 µm, about 100 µm, about 110 µm, about 120 µm, about 130 µm, about 140 µm or about 150 µm.

In a particular embodiment, the D50 of particle size of the moxidectin microspheres is about 110 µm.

In a particular embodiment, the D90 of particle size is about 100 µm, about 130 µm, about 150 µm, about 175 µm, about 200 µm, or about 250 µm.

In a particular embodiment, the D10 of the isoxazoline compound particle size is about 20 to 35 pm, the D50 of the particle size is about 90 to 105 µm and the D90 of the particle size is about 155 to 175 µm.

In a particular embodiment, for moxidectin microspheres the D10 of the particle size is about 60 to 85 µm, the D50 of the particle size is about 90 to 115 µm and the D90 of the particle size is about 145 to 165 µm.

In a particular embodiment, for the moxidectin microspheres the D10 of the particle size is about 80µm, the D50 of the particle size is about 110 µm and the D90 of the particle size is about 150 pm.

In a particular embodiment, the D10 of the particle size is about 25 to 30 µm, the D50 of the particle size is about 95 to 100 µm and the D90 of the particle size is about 160 to 170 µm.

In a particular embodiment, the D10 of the particle size is about 10 to 20 µm, the D50 of the particle size is about 85 to 110 µm and the D90 of the particle size is about 170 to 185 µm.

In a particular embodiment, the D10 of the particle size is about 10 to 15 µm, the D50 of the particle size is about 95 to 105 µm and the D90 of the particle size is about 175 to 180 µm.

In a particular embodiment, the D10 of the particle size is about 10 to 25 µm, the D50 of the particle size is about 40 to 60 µm and the D90 of the particle size is about 95 to 100 µm.

In a particular embodiment, the D10 of the particle size is about 15 to 20 µm, the D50 of the particle size is about 45 to 55 µm and the D90 of the particle size is about 90 to 95 µm.

In a particular embodiment, the D10 of the particle size is about 30 to 50 µm and the D50 of the particle size is about 70 to 130 µm.

In a particular embodiment, the D10 of the particle size is about 35 to 45 µm and the D50 of the particle size is about 90 to 110 µm.

In a particular embodiment, the D10 of the particle size is about 40 µm and the D50 of the particle size is about 100 µm.

The volume weighted particle size can be measured by sieving, microscopy or laser diffraction (Malvern or Sympatec).

The volume weighted particle size measurement can be performed with a Malvem Mastersizer 2000 with the Hydro 2000G measuring cell, or with a Horiba LA-910 laser scattering particle size distribution analyzer. The volume weighted particle size can be measured by a Sympatec Helos instrument.

For use in the invention, the isoxazoline compound is present in the pharmaceutical composition according to the invention in an amount of between about 0.1 and about 50% w/v of the final pharmaceutical composition according to the invention.

The isoxazoline is present in an amount of between about 10 and about 45% w/v; about 20 and about 45% w/v; about 15 and 35% w/v or about 25% w/v and about 35% w/v of or about 1% w/v and about 12% w/v of or about 3% w/v and about 9% w/v the pharmaceutical composition according to the invention.

In an embodiment of the invention and/or embodiments thereof, the composition comprises eprinomectin as (a1) physiologically active macrocyclic lactone and fluralaner, preferably (S)-fluralaner, as (b) isoxazoline compound of Formula (I).

In an embodiment of the invention and/or embodiments thereof, the composition comprises milbemycin oxime as (a) physiologically active macrocyclic lactone and fluralaner, preferably (S)-fluralaner, as (b) isoxazoline compound of Formula (I).

In an embodiment of the invention and/or embodiments thereof, the composition comprises selamectin as (a) physiologically active macrocyclic lactone and fluralaner, preferably (S)-fluralaner, as (b) isoxazoline compound of Formula (I).

In an embodiment of the invention and/or embodiments thereof, the composition comprises moxidectin as (a) physiologically active macrocyclic lactone and afoxolaner, preferably (S)-fluralaner, as (b) isoxazoline compound of Formula (I).

In an embodiment of the invention and/or embodiments thereof, the composition comprises eprinomectin as (a) physiologically active macrocyclic lactone and afoxolaner, preferably (S)-afoxolaner, as (b) isoxazoline compound of Formula (I).

In an embodiment of the invention and/or embodiments thereof, the composition comprises milbemycin oxime as (a) physiologically active macrocyclic lactone and afoxolaner, preferably (S)-afoxolaner, as (b) isoxazoline compound of Formula (I).

In an embodiment of the invention and/or embodiments thereof, the composition comprises selamectin as (a physiologically active macrocyclic lactone and afoxolaner, preferably (S)-afoxolaner, as (b) isoxazoline compound of Formula (I).

In an embodiment of the invention and/or embodiments thereof, the composition comprises moxidectin as (a) physiologically active macrocyclic lactone and afoxolaner, preferably (S)-afoxolaner, as (b) isoxazoline compound of Formula (I).

In an embodiment of the invention and/or embodiments thereof, the composition comprises eprinomectin as (a) physiologically active macrocyclic lactone and sarolaner as (b) isoxazoline compound of Formula (I).

In an embodiment of the invention and/or embodiments thereof, the composition comprises milbemycin oxime as physiologically active macrocyclic lactone and sarolaner as (b) isoxazoline compound of Formula (I).

In an embodiment of the invention and/or embodiments thereof, the composition comprises selamectin as) physiologically active macrocyclic lactone and sarolaner as (b) isoxazoline compound of Formula (I).

In an embodiment of the invention and/or embodiments thereof, the composition comprises moxidectin as physiologically active macrocyclic lactone and sarolaner as (b) isoxazoline compound of Formula (I).

In an embodiment of the invention and/or embodiments thereof, the composition comprises eprinomectin as physiologically active macrocyclic lactone and lotilaner as (b) isoxazoline compound of Formula (I).

In an embodiment of the invention and/or embodiments thereof, the composition comprises milbemycin oxime as physiologically active macrocyclic lactone and lotilaner as (b) isoxazoline compound of Formula (I).

In an embodiment of the invention and/or embodiments thereof, the composition comprises selamectin as physiologically active macrocyclic lactone and lotilaner as (b) isoxazoline compound of Formula (I).

In an embodiment of the invention and/or embodiments thereof, the composition comprises moxidectin as physiologically active macrocyclic lactone and lotilaner as (b) isoxazoline compound of Formula (I).

Injectable compositions generally need to be sterilized prior to administration to an animal. In a preferred embodiment of the invention and/or embodiments thereof, the microspheres are sterilized, for example with gamma radiation or electron beam irradiation.

Though physiologically active macrocyclic lactones are reported to degrade and lose much of the biological activity when irradiated, the microspheres (a) can be sterilized for injection by irradiation without the stability of the active ingredients being negatively impacted.

In an embodiment, the amount of isoxazoline compound in the pharmaceutical composition according to the invention is about 30% w/v of the pharmaceutical composition according to the invention.

In an embodiment, the amount of isoxazoline compound in the pharmaceutical composition according to the invention is about 7.5% w/v of the pharmaceutical composition according to the invention.

In one embodiment, the pharmaceutical composition must be reconstituted prior to injection.

For example, the pharmaceutical composition is reconstituted in an aqueous liquid carrier prior to injection.

In another embodiment, the pharmaceutical composition is a ready to use composition ready for injection.

In an embodiment, the pharmaceutical composition is administered in combination with an additional therapeutic agent.

The administration of the additional therapeutic agent may be in the same composition or in separate compositions.

The additional therapeutic agent may be a parasiticide or a vaccine.

In another embodiment, the additional therapeutic agent is another parasiticide. The other active ingredients are selected from the group consisting of isoxazoline compounds, macrocyclic lactones, avermectins (e.g., ivermectin, selamectin, doramectin, abamectin, and eprinomectin); milbemycins (milbemycin oxime); pro-benzimidazoles (e.g., febantel, netobimin, and thiophanate); benzimidazole derivatives, such as a thiazole benzimidazole derivatives (e.g., thiabendazole and cambendazole), carbamate benzimidazole derivatives (e.g., fenbendazole, albendazole (oxide), mebendazole, oxfendazole, parbendazole, oxibendazole, flubendazole, and triclabendazole); imidazothiazoles (e.g., levamisole and tetramisole); tetrahydropyrimidine (morantel and pyrantel), salicylanilides (e.g., closantel, oxyclozanide, rafoxanide, and niclosamide); nitrophenolic compounds (e.g., nitroxynil and nitroscanate); benzenedisulfonamides (e.g., clorsulon); pyrazinoisoquinolines (e.g., praziquantel and epsiprantel); heterocyclic compounds (e.g., piperazine, diethylcarbamazine, and phenothiazine); dichlorophen, arsenicals (e.g., thiacetarsamide, melorsamine, and arsenamide); cyclooctadepsipeptides (e.g., emodepside); paraherquamides (e.g. derquantel); and amino-acetonitrile compounds (e.g. monepantel, AAD 1566); amidine compounds (e.g., amidantel and tribendimidin), including all pharmaceutically acceptable forms, such as salts, solvates or N-oxides.

An embodiment of the invention is a method of treating or preventing a parasite infestation in an animal comprising administering to an animal in need thereof an effective amount of the injectable pharmaceutical compositions described above.

In an embodiment, the animal suffers minimal injection site irritation.

As noted above, minimal injection site irritation means injection site irritation that is less than 2×2 cm that persists for less than two to three days.

In an embodiment, the animal is a companion animal. In an embodiment, the companion animal is a dog or cat.

The optimum effective amount to be employed for best results will, of course, depend upon the particular isoxazoline compound employed, the species of animal to be treated, and the type and severity of parasitic infection or infestation.

Generally good results are obtained with isoxazoline compounds of formula (I) when administered from about 0.01 and 200 mg/kg body weight of the animal, in one embodiment 0.1 to 100 mg per kg of animal body weight, or 0.5 to 50 mg per kg of animal body weight or 1 to 30 mg per kg of animal body weight such total dose being given at one time or in divided doses.

Generally good results are obtained with moxidectin when administered from about 0.01 and 10 mg/kg body weight of the animal, in one embodiment 0.1 to 5 mg per kg of animal body weight, such total dose being given at one time or in divided doses.

The injectable pharmaceutical compositions may be administered daily, weekly, monthly, semiannually or annually.

The injectable pharmaceutical compositions may be administered every month, every two months, every three months, every four months, every five months, every 6 months, every seven months, eight months, every nine months, every ten months, every eleven months, every twelve months, every 13 months, every 14 months, every 15 months, every 16 months, every 17 months or every 18 months.

Especially preferred is an administration every 6 months.

Preferred is also an administration every 12 months. This provides a long-term protection of animals from both ectoparasites, especially fleas and ticks, and endoparasites, especially heartworm and/or gastrointestinal helminths. Especially preferred is long term protection against heartworm infestation.

Of benefit is the possibility to apply the injectable composition of the invention together with the annual vaccination against infectious diseases such as distemper, influenza, rabies and other vaccines with conventional antigens.

An embodiment of the injectable pharmaceutical composition, the D50 of particle size of the isoxazoline compound and/or moxidectin microspheres is from about 75 microns to about 130 microns and the D10 of the particle size is from about 30 microns to about 100 microns.

An embodiment of the invention is a kit for treating or preventing a parasite infestation in an animal, the kit comprising two or more containers:

a) solid crystalline isoxazoline compound and moxidectin microspheres;

b) a vehicle comprising a pharmaceutically acceptable excipient capable of forming a suspension with the compounds of a); and c) instructions for combining the solid crystalline isoxazoline compound and moxidectin microspheres with the aqueous liquid vehicle prior to injection.

wherein for the solid crystalline isoxazoline compound and the moxidectin microspheres, the D50 of particle size is from about 75 microns to about 130 microns and the D10 of the particle size is from about 30 microns to about 50 microns.

In another embodiment, the isoxazoline compound is fluralaner.

An embodiment of the invention is a kit, wherein the kit comprises:

a) a first container comprising a solid mixture of particles of isoxazoline compound of Formula (I) as described in claims 1, 8, 9, 10, 11, 12, 17 and 18 and moxidectin microspheres as described in claims 1 to 12 and;
b) a second container with an aqueous carrier comprising one or more suspending agents, wetting agents and/or preservatives and water; and
c) instructions for reconstituting moxidectin microspheres and isoxazoline compound particles with the aqueous carrier prior to subcutaneous or intramuscular injection to the animal.

In one embodiment the first container comprises an effective amount of moxidectin and of the isoxazoline compound of Formula (I) as described above, that is sufficient for treating and/or preventing a parasite infestation of an animal.

In one embodiment the kit further comprises an apparatus for reconstituting and parenterally (by injection) administering a mixture of the composition from the first and second container to an animal, especially using a syringe (e.g. 18 gauge).

In one embodiment in the first container the isoxazoline compound of Formula (I) and the moxidectin microspheres have a volume weighted particle size distribution D50 of about 25 microns to about 250 microns as measured by a static light scattering instrument.

In another embodiment in the first container the D10 of the particle size of the isoxazoline compound is about 20 to 35 μm, the D50 of the particle size is about 90 to 105 μm and the D90 of the particle size is about 155 to 175 μm.

Another aspect of the current invention is a method of treating or preventing a parasite infestation in an animal comprising administering to an animal in need thereof the injectable veterinary composition.

Another aspect of the current invention is a method of producing the injectable veterinary composition according to the invention comprising the steps of:

a) Preparing isoxazoline compound particles by crystallization;
b) Preparing moxidectin microspheres by melting the fat, wax or mixture thereof and adding the moxidectin and optionally an antioxidant and preparing microspheres through spinning disk atomization and sieving;
c) filling the moxidectin microspheres obtained by step b) together with the isoxazoline particles obtained by step a) in a first container;
d) preparing the aqueous carrier by dissolving the excipients including suspending agents, wetting agents and/or preservatives in water and filling into a second container;
e) reconstituting the solids by transferring the aqueous carrier from the second container d) to the first container c) and shake to form a.

Spinning disk has been identified as a production technique for generation of uniform spherical particles with low particle size distribution span through control of critical process parameters such as melt temperature, flow rate, and disk speed.

Spinning disk atomization is an encapsulation technique that uses mechanical energy to pressurize the liquid film or increase it kinetic energy for possible disintegration in the form of droplets.

Alternatively, other methods such as hot melt extrusion, hot melt granulation, thin-film evaporation, etc. may be used to incorporate the moxidectin homogenously into the fat, wax, or mixture thereof. The resulting mixture could be milled or sprayed to reach the desired particle size.

If desired sieving of the material to prepare a batch with defined particle size can be performed.

In other words, the microspheres (a) can be regarded as microspheres prepared by incorporating the physiologically active macrocyclic lactone and then forming microspheres of the resulting mixture by a variety of techniques such as the ones indicated above.

Alternatively, the mixture of the physiologically active macrocyclic lactone and optionally other excipients may be cooled to give a solid which may then be processed by procedures such as milling, grinding and the like.

Generally, solvent evaporation, spinning disk atomization, spray drying as well as sieving are methods known to skilled person.

In one embodiment of the invention and/or embodiments thereof, the mixture in the first container comprises an effective amount of microspheres as described in any one of claims 1 to 14 and particles of an isoxazoline compound of Formula (I) as described in any one of claims 1 to 14 and/or a compound of Formula (II) as described in any one of claims 1 to 14 that is sufficient for treating or preventing a parasite infestation of an animal.

In one embodiment of the invention and/or embodiments thereof the kit further comprises an apparatus for reconstituting and parenterally administering a mixture of the composition from the first and second container to an animal, especially a syringe.

Another embodiment is a method of treating and/or preventing a parasite infestation in an animal for a prolonged period of 6 or alternatively 12 months, comprising administering to an animal in need thereof the reconstituted liquid that is prepared when using the kit as described above and administer it to the animals according to the instructions by injection.

The parasites are ectoparasites and endoparasites as described earlier.

The preferred target animals are companion animals such as cats or dogs, especially dogs.

The optimum effective amount to be employed for the best results will, of course, depend on the particular isoxazoline compound as well as the physiologically active macrocyclic lactone employed, the species of animal to be treated and the type and severity of parasitic infection or infestation.

In a preferred embodiment of the invention and/or embodiments thereof, the isoxazoline compound of Formula (I), preferably fluralaner, is administered at about 0.01 to about 200 mg/kg body weight of the animal, preferably from about 0.1 to about 100 mg per kg of animal body weight, more preferably from about 0.5 to about 50 mg per kg of animal body weight, in particular from about 1 to about 30 mg per kg of animal body weight. The total dose can be given at once or in divided doses.

In a preferred embodiment of the invention and/or embodiments thereof, the physiologically active macrocyclic lactone, preferably moxidectin is administered at about 0.01 to about 10 mg/kg body weight of the animal, preferably from about 0.1 to about 5 mg per kg of animal body weight. The total dose can be given at once or in divided doses.

It turned out that when the present injectable veterinary composition is used in treating and/or preventing a parasite infestation in an animal, the treated animal suffers minimal injection site irritation.

As noted above, minimal injection site irritation means injection site irritation that is less than 2×2 cm that persists for less than two to three days.

Another aspect of the present invention is a method for treating and/or preventing a parasite infestation in an animal comprising administering to a subject in need thereof a therapeutically effective amount of the injectable veterinary composition according to the present invention or the kit according to the present invention Again, as far as the injectable veterinary composition and the kit are concerned, the same applies as described above. The same applies to parasites and parasite infestation.

Features of the invention have been described in embodiments in the present application; however, for brevity not all combinations of the features are literally described.

Combinations of features as described above are, however, expressly considered to be part of the invention.

EXAMPLES

Example 1

Preparation of 10% Moxidectin Microspheres

10% Moxidectin in Glyceryl tristearate (GTS) microspheres were manufactured by spinning disk with the formulation below:

TABLE 1

Example Formulation of 10% Moxidectin in Glyceryl Tristearate Microspheres

| Ingredient | % w/w |
|---|---|
| Moxidectin | 10.00 |
| Glyceryl Tristearate | 89.97 |
| Butylated Hydroxytoluene | 0.03 |

Briefly, 180 g of Glyceryl tristearate was melted in a vessel and heated to a temperature of 180° C. with stirring. 20 g of Moxidectin and 0.06 g of Butylated Hydroxytoluene were added and stirred until dissolved. The resulting molten solution was cooled to ~80° C. and pumped on to a 4" disk heated to ~90° C. at 3000 RPM. The resulting microspheres were sieved and material less than 150 μm was collected for further characterization and study.

Example 2

Sterilization of 10% Moxidectin in GTS Microspheres-Stability of Microspheres to Irradiation The microsphere compositions listed below are placed in 20 mL serum vials, two of which are flushed with dry nitrogen gas to remove oxygen. The vials are then closed with elastomeric septums and crimped aluminum caps. Next, the microspheres are irradiated 15, 20, and 25 kGy irradiation by both gamma irradiation and electron-beam for sterilization. The microspheres are extracted into acetonitrile/water (1:1 and analyzed for 23-(O-methyloxime)-F28249a by high performance liquid chromatography. The results of this experiment are summarized below in Table 2. GTS Microspheres were sterilized at either cold temperature or room temperature and with or without a Nitrogen overlay.

Samples were assessed for changes in assay. % assay is reported as % of non-irradiated assay.

TABLE 2

Effect of Type of Irradiation, Irradiation Dose, Temperature, and Nitrogen Overlay on Moxidectin Assay During Sterilization

| Electron Beam | | | | | Gamma Irradiation | | | | |
|---|---|---|---|---|---|---|---|---|---|
| Microsphere Lot | Dose (kGy) | Temperature | Sparge | Assay | Microsphere Lot | Dose (kGy) | Temperature | Sparge | Assay |
| 10% | 15 | Ambient | not sparged | 96.80 | 10% | 15-18 | Ambient | not sparged | 92.19 |
| Moxidectin | | | nitrogen overlay | 95.64 | Moxidectin | | | nitrogen overlay | 91.36 |
| Microspheres | | 5° C. | not sparged | 93.27 | Microspheres | | 5° C. | not sparged | 89.37 |
| | | | nitrogen overlay | 93.99 | | | | nitrogen overlay | 88.93 |
| | 20 | Ambient | not sparged | 95.33 | | 20-24 | Ambient | not sparged | 87.70 |
| | | | nitrogen overlay | 96.41 | | | | nitrogen overlay | 87.16 |
| | | 5° C. | not sparged | 93.60 | | | 5° C. | not sparged | 86.59 |
| | | | nitrogen overlay | 93.67 | | | | nitrogen overlay | 85.23 |
| | 25 | Ambient | not sparged | 95.02 | | 25-30 | Ambient | not sparged | 86.90 |
| | | | nitrogen overlay | 94.82 | | | | nitrogen overlay | 85.42 |
| | | 5° C. | not sparged | 92.93 | | | 5° C. | not sparged | 84.98 |
| | | | nitrogen overlay | 93.71 | | | | nitrogen overlay | 85.33 |
| Moxidectin | 15 | Ambient | not sparged | 96.08 | Moxidectin | 15-18 | Ambient | not sparged | 97.18 |
| Drug | | | nitrogen overlay | 94.98 | Drug | | | nitrogen overlay | 97.69 |
| Substance | | 5° C. | not sparged | 93.42 | Substance | | 5° C. | not sparged | 95.59 |
| | | | nitrogen overlay | 93.06 | | | | nitrogen overlay | 95.76 |
| | 20 | Ambient | not sparged | 95.31 | | 20-24 | Ambient | not sparged | 95.51 |
| | | | nitrogen overlay | 95.91 | | | | nitrogen overlay | 96.67 |
| | | 5° C. | not sparged | 94.07 | | | 5° C. | not sparged | 94.30 |
| | | | nitrogen overlay | 94.03 | | | | nitrogen overlay | 93.64 |
| | 25 | Ambient | not sparged | 94.94 | | 25-30 | Ambient | not sparged | 95.23 |
| | | | nitrogen overlay | 95.11 | | | | nitrogen overlay | 96.03 |
| | | 5° C. | not sparged | 93.15 | | | 5° C. | not sparged | 93.13 |
| | | | nitrogen overlay | 93.48 | | | | nitrogen overlay | 95.06 |

Example 3

Preparation of Liquid Aqueous Vehicle

Approximately 50% of the water for injection was charged to a vessel and heated to about 70-80° C., and the suspending agent NaCMC, Hypromellose E50 or PVP is added and homogenized until dissolved. The other ingredients were added slowly and mixed with stirring to achieve dispersion. The heat was removed and cold water for injection added to bring the volume to 10 liters. In Example 3B and 3D the pH was adjusted to 4.5-5.5 by adding HCl.

Each vehicle was the sterilized by autoclaveand the vehicle solution was stored in sterile containers.

Dose Uniformity of the Product-Ready to Use Injectable Suspension

While Moxidectin microspheres and Fluralaner particles show similar particle size, their densities vary. Therefore, a number of different vehicles were tested in order to find a vehicle suitable for uniform resuspension and dosing.

Samples containing 15% Fluralaner and 1.7% Moxidectin GTS Microspheres were shaken by hand until visually dispersed in each vehicle, ~30 seconds.

The following vehicles were investigated:

Example Formulations of Viscous Aqueous Vehicles for Reconstitution/Resuspension Example 3A

| Ingredients | % w/w |
|---|---|
| Sodium CMC | 2.2 |
| Poloxamer 124 | 0.11 |
| Benzyl alcohol | 2.2 |
| Water for injection (WFI)I | QS |

Example 3B

| Ingredients | % w/w |
|---|---|
| Sodium CMC | 2.2 |
| Poloxamer 124 | 0.11 |
| Sodium phosphate (dibasic dihydrate) | 0.77 |
| Benzyl alcohol | 2.2 |
| HCl | 0.17 |
| WFI | QS |

Example 3C

| Ingredients | % w/w |
|---|---|
| Polyvinylpyrrolidone K90 | 7.5 |
| Poloxamer 124 | 0.11 |
| Benzyl alcohol | 2.2 |
| WFI | QS |

Example 3D

| Ingredients | % w/w |
|---|---|
| Polyvinylpyrrolidone K90 | 7.5 |
| Poloxamer 124 | 0.11 |
| Sodium phosphate (dibasic dihydrate) | 0.77 |
| Benzyl alcohol | 2.2 |
| HCl | 0.17 |
| WFI | QS |

Example 3E

| Ingredients | % w/w |
|---|---|
| Hypromellose E50 | 2.5 |
| Sodium Chloride | 0.9 |
| Methylparaben | 0.18 |
| Propylparaben | 0.02 |
| WFI | QS |

6 1 mL samples were then drawn and tested for moxidectin and fluralaner assay with results shown in Table 4 below:

TABLE 4

| Vehicle Formulation | Moxidectin Assay % | Moxidectin RSD % | Fluralaner Assay % | Fluralaner RSD % |
|---|---|---|---|---|
| Example 3A | 106.10 | 5.58 | 99.83 | 6.41 |
| Example 3B | 108.99 | 8.32 | 97.19 | 9.65 |
| Example 3C | 106.00 | 5.29 | 100.45 | 2.84 |
| Example 3D | 106.20 | 5.39 | 98.45 | 5.45 |
| Example 3E | 94.12 | 12.78 | 85.83 | 15.42 |

Example 4

Making and Using the Final Formulation

At the point of use, the vehicle made in Example 3 was added to the moxidectin microspheres and crystalline fluralaner particles made in Example 1 and the container was shaken to disperse the microspheres and fluralaner particles in the liquid vehicle. The formulation was then drawn into a syringe in a dose volume specified for the body weight of the dog to be treated and injected subcutaneously.

Example 5

Pharmacokinetic Assessment of Injectable Formulations Comprising GTS Moxidectin Microspheres and Fluralaner Particles Formulations:

A. 15% Fluralaner+0.17% Moxidectin Microspheres (unsieved, GTS, 25 kGy)

B. 15% Fluralaner+0.17% Moxidectin Microspheres (unsieved, GTS, 15 kGy)

C. 15% Fluralaner+0.17% Moxidectin Microspheres (D50=75 μm, GTS, 25 kGy)

D. 15% Fluralaner+0.17% Moxidectin Microspheres (D50=150 μm GTS, 25 kGy)

The formulations were prepared as following:

A. The Vehicle

1. Charge ~80% of the total volume of water for injection.
2. The suspending agent (Sodium carboxy methyl cellulose (NaCMC)) was added and mixed with an overhead mixer for ~5 minutes.
3. The mixture was further mixed with a homogenizer until free of agglomerates
4. The wetting agent (Poloxamer 124) was added and mixed with an overhead mixer until uniform.
5. The preservative (Benzyl alcohol (BA)) was added and mixed with an overhead mixer until uniform.
6. Sodium phosphate was added and mixed with an overhead mixer until uniform.
7. The antifoaming agent (Simethicone) was mixed gently with an overhead mixer until uniform (5 minutes).
8. The pH of the mixture was adjusted to pH 7.0-7.4 with the addition of HCl. Mix gently with an overhead mixer until uniform (5 min).
9. Water was added QS to final weight for injection and then mixed gently with an overhead mixer until uniform (5 min).
10. The resulting formulation was packaged into injectable vials and sealed with stopper.
11. The vials were autoclaved for a cycle of 15 minutes at 121° C.

B. The Active Ingredients 1. solid fluralaner and moxidectin GTS microspheres (prepared as described above) were added to a vial and sealed.
2. The vial was terminally sterilized by gamma radiation.

C. Formation of the Reconstituted Injectable Formulation

1. The vehicle of vial of A was added to the active ingredient vial of B and shaken
2. The resultant suspension was ready for injection.

Analogous procedures were used to produce the formulations of Examples 5B-H. Batch sizes ranged from 50 mL to 1000 mL.

Vehicle for all formulations:

| Ingredients | % w/w |
|---|---|
| Sodium CMC | 2.2 |
| Poloxamer 124 | 0.11 |
| Sodium phosphate (dibasic dihydrate) | 0.77 |
| Benzyl alcohol | 2.2 |
| HCl | 0.19 |
| WFI | QS |

Samples of Formulations A, B, C or D were administered subcutaneously on a single occasion at 0.1 mL/kg BW (i.e. 15 mg fluralaner/kg BW, 0.17 mg moxidectin/kg BW) to different groups of eight Beagle dogs each.

The local tolerance of the formulations was assessed for at least 21 days after administration.

Blood samples for determination of moxidectin and total fluralaner plasma concentrations were collected prior to treatment, at 8 hours, and at 1, 3, 5, 7, 10, 14, 21, 28, 35, 42, 49, 56, 70, 84, 98, 112, 126, 140, 154, 168, and 182 days post-treatment.

A favorable pharmacokinetic profile showing prolonged plasma levels of moxidectin and fluralaner in dogs after sc administration was obtained for all test formulations.

There were no significant injection reactions during the evaluation of the formulations of Example 5.

The invention claimed is:

1. An injectable veterinary composition comprising a) moxidectin microspheres comprising from about 50% to about 99% by weight of a fat, wax or mixture thereof, and 0.01-10% by weight of an anti-oxidant; and b) particles of an isoxazoline compound wherein the isoxazoline compound is fluralaner wherein the moxidectin microspheres and isoxazoline compound particles are suspended in an aqueous carrier comprising one or more suspending agents selected from sodium carboxymethylcellulose, polyvinylpyrrolidone and methylcellulose, one or more wetting agents comprising a poloxamer, and water and optionally one or more preservatives.

2. The injectable veterinary composition of claim 1 wherein the fat, wax or mixture thereof has a melting point of higher than about 40° C.

3. The injectable veterinary composition of claim 1 wherein the moxidectin microspheres comprise from about 75% to about 95% by weight of the fat, wax or mixture thereof.

4. The injectable veterinary composition according to claim 1 wherein said fat, wax or mixture thereof comprises a fatty acid ester.

5. The injectable veterinary composition according to claim 4 wherein said fatty acid ester is glyceryl tristearate.

6. The injectable veterinary composition according to claim 1 in which the moxidectin microspheres and/or isoxazoline compound particles have a volume weighted particle size distribution D50 as measured by a static light scattering instrument of from about 25 μm to about 250 μm.

7. The injectable veterinary composition according to claim 6 wherein the moxidectin microspheres or isoxazoline compound particles size distribution D50 is from about 75 μm to about 150 μm.

8. The injectable veterinary composition according to claim 1 in which the isoxazoline compound particles have a thickness of greater than 10 μm but less than 100 μm, as measured by scanning electron microscopy.

9. The injectable veterinary composition according to claim 8 wherein the isooxazoline compound particles have a thickness of greater than 30 μm but less than 80 μm.

10. The injectable veterinary composition of claim 1, wherein the D10 of the volume weighted particle size of the moxidectin microspheres or the isoxazoline compound particles as measured by a static light scattering instrument is about 20 to 35 μm, the D50 of the particle size is about 90 to 105 μm and the D90 of the particle size is about 155 to 175 μm.

11. The injectable veterinary composition of claim 1, wherein the wetting agent is a poloxamer.

12. A kit, wherein the kit comprises:

a) a first container comprising a solid mixture of particles of isoxazoline compound wherein the isoxazoline compound is fluralaner and moxidectin microspheres comprising from about 50% to about 99% by weight of a fat, wax or mixture thereof, and 0.01-10% by weight of an anti-oxidant and;

b) a second container with an aqueous carrier comprising one or more suspending agents wherein the suspending agent is selected from sodium carboxymethylcellulose, polyvinylpyrrolidone and methylcellulose, one or more wetting agents comprising poloxamer, and water and optionally preservatives; and c) instructions for reconstituting moxidectin microspheres and isoxazoline compound particles with the aqueous carrier prior to subcutaneous or intramuscular injection to the animal.

13. The kit according to claim 12, wherein the first container comprises an effective amount of moxidectin and of the isoxazoline compound that is sufficient for treating or preventing a parasite infestation of an animal.

14. The kit according to claim 12, wherein the kit further comprises an apparatus for reconstituting and parenterally administering a mixture of the composition from the first and second container to an animal.

15. The kit according to claim 14, wherein the apparatus comprises a syringe.

16. The kit according to claim 12 wherein in the first container the isoxazoline compound and/or the moxidectin microspheres have a volume weighted particle size distribution D50 of about 25 microns to about 250 microns as measured by a static light scattering instrument.

17. The kit according to claim 12 wherein in the first container the D10 of the particle size of the isoxazoline compound is about 20 to 35 μm, the D50 of the particle size is about 90 to 105 μm and the D90 of the particle size is about 155 to 175 μm.

18. A method of treating or preventing a parasite infestation in an animal comprising administering to the animal in need thereof the injectable veterinary composition of claim 1.

19. A method of producing the injectable veterinary composition according to claim 1 comprising the steps of:

a) Preparing isoxazolines particles;

b) Preparing the moxidectin microspheres by melting the fat, wax or mixture thereof and adding the moxidectin and optionally an antioxidant and preparing the microspheres through spinning disk atomization and sieving;

c) filling the moxidectin microspheres obtained by step b) together with the isoxazoline particles obtained by step a) in a first container;

d) preparing the aqueous carrier by dissolving the excipients including the suspending agents, wetting agents and/or preservatives in water and filling into a second container;

e) reconstituting the solids by transferring the aqueous carrier from the second container d) to the first container c) and shake to form a ready-to-use suspension.

* * * * *